(12) United States Patent
Grill et al.

(10) Patent No.: US 11,103,708 B2
(45) Date of Patent: Aug. 31, 2021

(54) SYSTEMS AND METHODS FOR DETERMINING OPTIMAL TEMPORAL PATTERNS OF NEURAL STIMULATION

(71) Applicant: Duke University, Durham, NC (US)

(72) Inventors: Warren M. Grill, Durham, NC (US); Isaac Cassar, Durham, NC (US); Nathan Titus, Durham, NC (US)

(73) Assignee: Duke University, Durham, NC (US)

( * ) Notice: Subject to any disclaimer, the term of this patent is extended or adjusted under 35 U.S.C. 154(b) by 325 days.

(21) Appl. No.: 16/303,812

(22) PCT Filed: Jun. 1, 2017

(86) PCT No.: PCT/US2017/035556
§ 371 (c)(1),
(2) Date: Nov. 21, 2018

(87) PCT Pub. No.: WO2017/210491
PCT Pub. Date: Dec. 7, 2017

(65) Prior Publication Data
US 2020/0316384 A1 Oct. 8, 2020

Related U.S. Application Data

(60) Provisional application No. 62/344,033, filed on Jun. 1, 2016.

(51) Int. Cl.
*A61N 1/36* (2006.01)
*G16H 20/40* (2018.01)
(Continued)

(52) U.S. Cl.
CPC ......... *A61N 1/36178* (2013.01); *A61N 1/025* (2013.01); *A61N 1/36139* (2013.01);
(Continued)

(58) Field of Classification Search
CPC ............... A61N 1/36178; A61N 1/025; A61N 1/36139; A61N 1/36185; A61N 1/37235;
(Continued)

(56) References Cited

U.S. PATENT DOCUMENTS

| 4,338,945 A | 7/1982 | Kosugi et al. |
| 5,716,377 A | 2/1998 | Rise et al. |

(Continued)

FOREIGN PATENT DOCUMENTS

| CN | 102521456 A | 6/2012 |
| JP | 2008506464 A | 3/2008 |

(Continued)

OTHER PUBLICATIONS

Decision of Refusal issued in counterpart Japanese Patent Application No. JP 2016-501846 dated Nov. 6, 2018 (four (4) pages).

(Continued)

*Primary Examiner* — Amanda K Hulbert
*Assistant Examiner* — Natasha Patel
(74) *Attorney, Agent, or Firm* — Olive Law Group, PLLC

(57) ABSTRACT

Systems and methods for determining optimal temporal patterns of neural stimulation are disclosed. According to an aspect, a method includes selecting a temporal pattern for neural stimulation. The method also includes determining a mutation type for altering a pattern of pulses of the temporal pattern. The method also includes identifying a location within the pattern of pulses of the temporal pattern to alter based on the determined mutation type. The method further includes altering the pattern of pulses of the temporal pattern based on the identified location and mutation type for application of the altered temporal pattern to a subject.

20 Claims, 21 Drawing Sheets

(51) Int. Cl.
*G16H 50/50* (2018.01)
*A61N 1/02* (2006.01)
*A61N 1/372* (2006.01)

(52) U.S. Cl.
CPC ..... *A61N 1/36185* (2013.01); *A61N 1/37235* (2013.01); *G16H 20/40* (2018.01); *G16H 50/50* (2018.01)

(58) Field of Classification Search
CPC .......... A61N 1/36167; A61N 1/36146; G16H 20/40; G16H 50/50
See application file for complete search history.

(56) References Cited

U.S. PATENT DOCUMENTS

| | | | |
|---|---|---|---|
| 6,560,490 | B2 | 5/2003 | Grill et al. |
| 6,944,501 | B1 | 9/2005 | Pless |
| 7,191,014 | B2 | 3/2007 | Kobayashi et al. |
| 7,463,927 | B1 | 12/2008 | Chaouat |
| 8,073,544 | B2 | 12/2011 | Pless |
| 2002/0052634 | A1 | 5/2002 | March |
| 2002/0169563 | A1 | 11/2002 | Ferreira |
| 2004/0111127 | A1 | 6/2004 | Gliner |
| 2004/0158298 | A1 | 8/2004 | Gliner et al. |
| 2005/0060009 | A1 | 3/2005 | Goetz |
| 2005/0222641 | A1 | 10/2005 | Pless |
| 2006/0015153 | A1 | 1/2006 | Gliner et al. |
| 2006/0149337 | A1 | 7/2006 | John |
| 2007/0106479 | A1 | 5/2007 | Geerts et al. |
| 2007/0191895 | A1 | 8/2007 | Foreman et al. |
| 2007/0265679 | A1 | 11/2007 | Bradley et al. |
| 2007/0288064 | A1 | 12/2007 | Butson et al. |
| 2008/0046036 | A1 | 2/2008 | King et al. |
| 2008/0215119 | A1 | 9/2008 | Woods et al. |
| 2009/0204173 | A1 | 8/2009 | Fang et al. |
| 2009/0279726 | A1 | 11/2009 | Baskent |
| 2009/0287271 | A1 | 11/2009 | Blum et al. |
| 2009/0326608 | A1 | 12/2009 | Huynh et al. |
| 2010/0152807 | A1 | 6/2010 | Grill et al. |
| 2010/0191307 | A1 | 7/2010 | Fang et al. |
| 2011/0040351 | A1 | 2/2011 | Butson et al. |
| 2011/0060383 | A1* | 3/2011 | Lineaweaver ......... G16H 50/50 607/57 |
| 2011/0087309 | A1 | 4/2011 | Stypulkowski |
| 2011/0213442 | A1 | 9/2011 | Pless |
| 2012/0136408 | A1 | 5/2012 | Grill et al. |
| 2012/0172946 | A1 | 7/2012 | Alataris et al. |
| 2012/0253421 | A1 | 10/2012 | Gliner et al. |
| 2013/0006331 | A1 | 1/2013 | Weisgarber et al. |
| 2013/0150922 | A1 | 6/2013 | Butson et al. |
| 2014/0163640 | A1 | 6/2014 | Edgerton et al. |
| 2014/0180361 | A1 | 6/2014 | Burdick et al. |
| 2015/0202446 | A1 | 7/2015 | Franke et al. |

FOREIGN PATENT DOCUMENTS

| | | |
|---|---|---|
| JP | 2011502586 A | 1/2011 |
| JP | 2012504458 A | 2/2012 |
| WO | 2006019764 A2 | 2/2006 |
| WO | 2010065888 A2 | 6/2010 |
| WO | 2009061813 A9 | 7/2010 |

OTHER PUBLICATIONS

Decision of Refusal issued in counterpart Japanese Patent Application No. JP 2016-501841 dated Mar. 18, 2019 (two (2) pages).
Communication under Rule 71(3) EPC issued in counterpart European Patent Application No. 15814864.3 dated Sep. 25, 2019 (fifty-nine (59) pages).
Non-Final Office Action issued in counterpart U.S. Appl. No. 14/774,160 dated Sep. 19, 2019.
Australian Examination Report for Application No. 2014244386 dated Jul. 24, 2017.
Australian Examination Report issued in counterpart Australian Application No. 2014244318 dated May 20, 2018 (three (3) pages).
Australian Full Examination Report for Application No. 2014244318 dated Aug. 16, 2017.
Benabid, A., et al, "Long-Term Suppression of Tremor by Chronic Stimulation of the Ventral Intermediate Thalamic Nucleus," Lancet. 337:403-6 (Feb. 16, 1991).
Birdno, M.J., "Analyzing the mechanisms of thalamic deep brain stimulation: computational and clinical studies," Ph. D. Dissertation, Department of Biomedical Engineering, Duke University, Durham, NC, USA (Aug. 2009).
Constantoyannis, C., et al, "Tremor induced by thalamic deep brain stimulation in patients with complex regional face pain," Movement Disorders vol. 19, No. 8, 19:933-936. (2004).
Corrected Notice of Allowability issued in counterpart U.S. Appl. No. 14/774,156 dated Dec. 26, 2018.
Davis, L, "Handbook of Genetic Algorithms" Van Nostrand Reinhold, NY (1991).
Dorval, A. D., et al., "Deep Brain Stimulation Alleviates Parkinsonian Bradykinesia by Regularizing Thalamic Throughput in Human Subjects,". Society for Neuroscience Abstracts 32. (2007), J Neurophysiol 104: 911-921 (Aug. 2010, First published May 26, 2010).
European Search Report and Opinion for European Patent Application No. 15814864.3 dated Jan. 8, 2018.
Extended European Search Report dated Nov. 3, 2016, received in EP Application No. 14776331.2.
Extended European Search Report for European patent application No. EP 14773114, dated Oct. 21, 2016. (seven 7) pages).
Feng, X., et al, "Optimal Deep Brain Stimulation of The Subthalamic Nucleus—A Computational Study," J Comput Veurosci. 23(3):265-282 (Jan. 19, 2007).
Final Office Action dated Aug. 10, 2012 in U.S. Appl. No. 12/587,295.
Final Office Action issued in counterpart U.S. Appl. No. 14/774,160 dated Feb. 7, 2019.
Fogelson, N. et al, "Frequency Dependent Effects of Subthalamic Nucleus Stimulation in Parkinson's Disease," Neuroscience Letters 382:5-9 (2005).
Grefenstette, J.J., "Optimization of Control Parameters for Genetic Algorithms," IEEE Transactions on Systems, Man and Cybernetics 16:122-128 (1986).
Grill, W.M. et al, "Effect of Stimulus Waveform on Tremor Suppression and Paresthesias Evoked by Thalamic Deep Brain Stimulation," Society for Neuroscience Abstracts 29 (2003).
International Preliminary Report on Patentability and Written Opinion issued in PCT Application No. PCT/US2017/035556 dated Dec. 4, 2018 (eight (8) pages).
International Search Report and the Written Opinion of the International Searching Authority in corresponding PCT application No. PCT/US09/05459 (dated Dec. 3, 2009).
International Search Report and Written Opinion for Application No. PCT/US2017/035556 dated Oct. 2, 2017.
Kuncel, A.M, et al, "Clinical Reponse To Varying The Stimulus Parameters In Deep Brain Stimulation For Essential Tremor," Movement Disorders 21(11):1920-1928 (2006).
Kupsch, A. et al, "The effects of frequency in pallidal deep brain stimulation for primary dystonia," J Neurol 250:1201-1204 (2003).
Limousin, P. et al, "Effect on Parkinsonian signs and symptoms of bilateral stimulation," The Lancet 345:91-95 (1995).
McIntyre, C.C., et al, "Cellular effects of deep brain stimulation: model-based analysis of activation and inhibition," J Neurophysiol 91:1457-1469 (2004).
Non-Final Office Action dated Mar. 9, 2012 in U.S. Appl. No. 12/587,295.
Non-Final Office Action for U.S. Appl. No. 15/321,801 dated Feb. 5, 2018.
Notice of Acceptance issued in counterpart Australian Application No. 2014244386 dated May 11, 2018 (three (3) pages).
Notice of Allowance dated Apr. 15, 2013 in U.S. Appl. No. 12/587,295.
Notice of Allowance issued in counterpart U.S. Appl. No. 14/774,156 dated Dec. 11, 2018.

(56) References Cited

OTHER PUBLICATIONS

Notice of Allowance issued in counterpart U.S. Appl. No. 15/321,801 dated May 25, 2018.
Notification of Transmittal of the International Search Report and the Written Opinion of the International Searching Authority, or the Declaration, PCT International Searching Authority, Aug. 6, 2014. (Fifteen (15) pages).
Notification of Transmittal of the International Search Report and the Written Opinion of the International Searching Authority, or the Declaration, PCT International Searching Authority, dated Jul. 3, 2014.
Office Action for Japanese Patent Application No. JP 2016-501841 dated Jan. 9, 2018.
Office Action for Japanese Patent Application No. JP 2016-501846 dated Feb. 27, 2018 (six (6) pages).
Office Action received in U.S. Appl. No. 14/774,160 dated Mar. 24, 2017.
Rubin, J.E. et al, "High Frequency Stimulation of the Subthalamic Nucleus Eliminates Pathological Thalamic Rhythmicity in a Computational Model,". J Comput Neurosci 16:211-235 (2004).
Second Office Action issued in counterpart Japanese Application No. 2016-501841 dated May 15, 2018 with English translation (eighteen (18) pages).
Supplemental European Search Report for European patent application No. EP 14773114, PCT/US2014/025389 dated Nov. 3, 2016.
Timmerman, L. et al, "The cerebral oscillatory network of parkinsonian resting tremor," Brain, 126:199-212 (2003).
U.S. Final Office Action for U.S. Appl. No. 14/774,160 dated Oct. 20, 2017.
Examination Report issued in counterpart Australian Application No. 2018217227 dated Jul. 16, 2019 (three (3) pages).
Examination Report No. 1 for Standard Patent Application for corresponding Australian Patent Application No. 2017275585 dated Jun. 11, 2021.

* cited by examiner

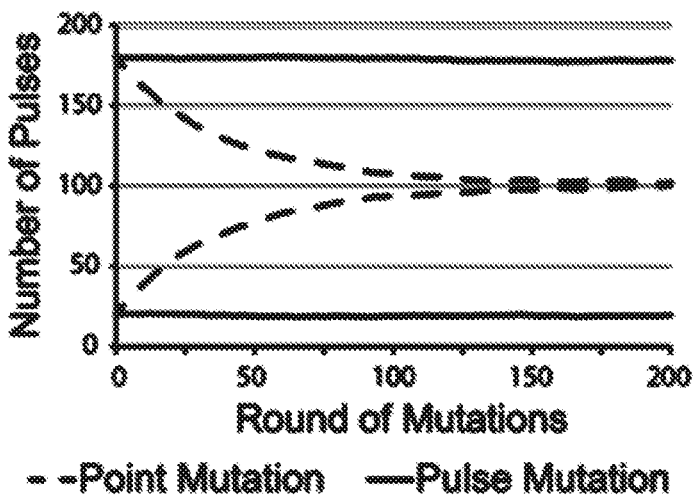
FIG. 12A
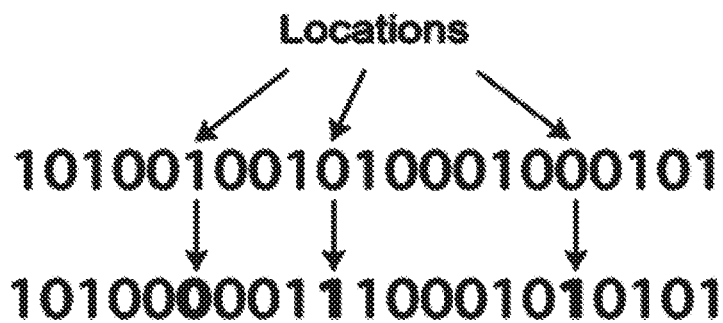
FIG. 12B
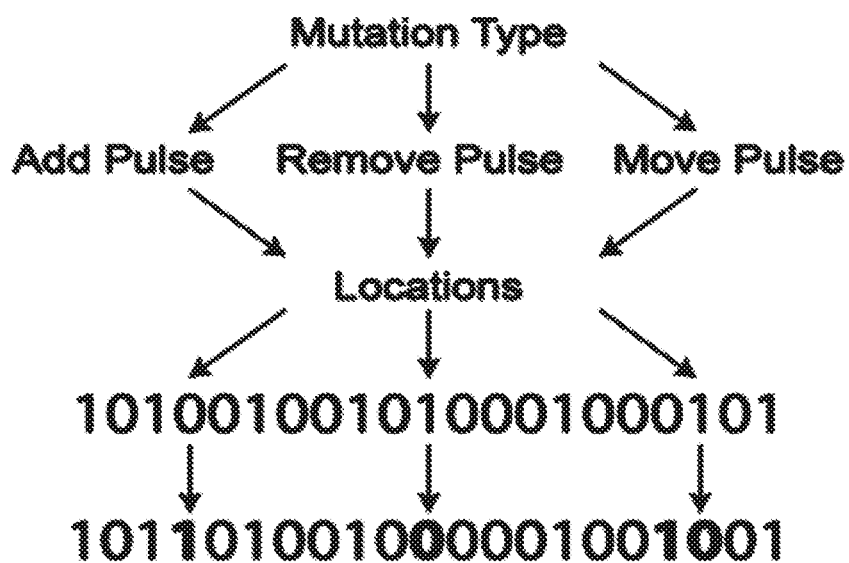

FIG. 13

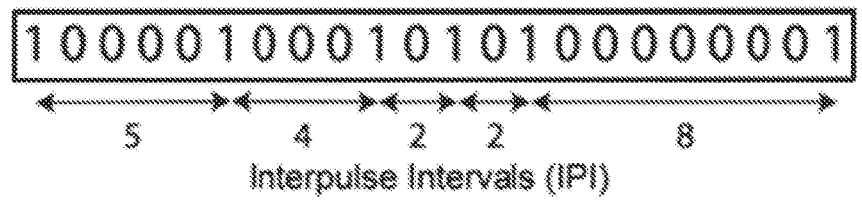
FIG. 21A
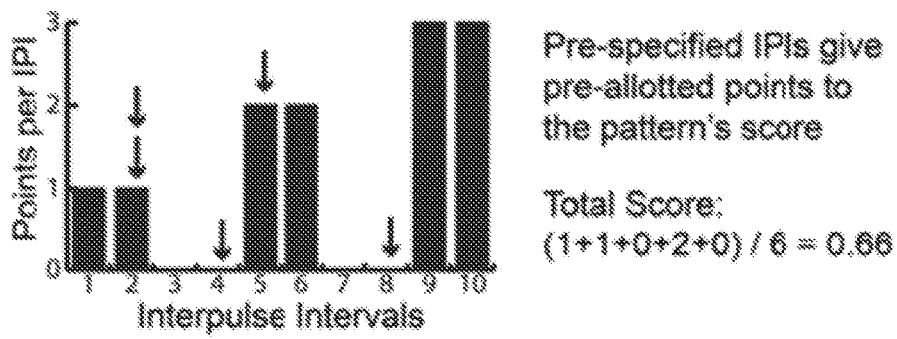
FIG. 21B
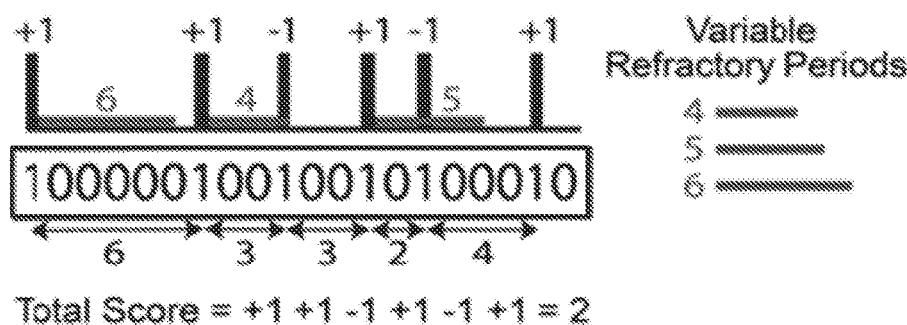
FIG. 21C
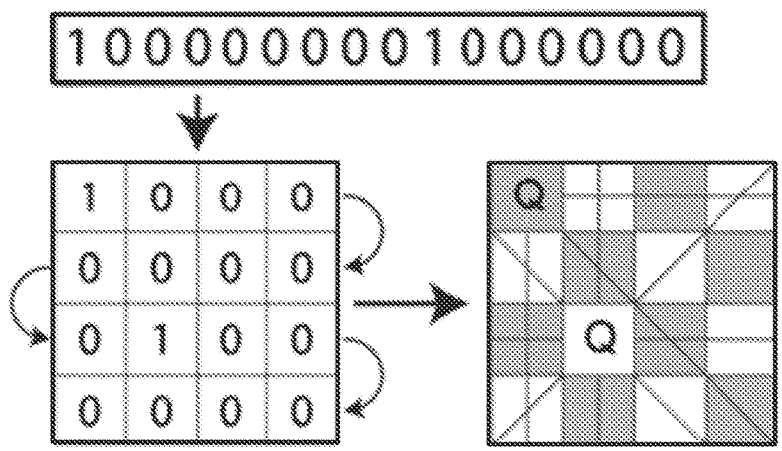

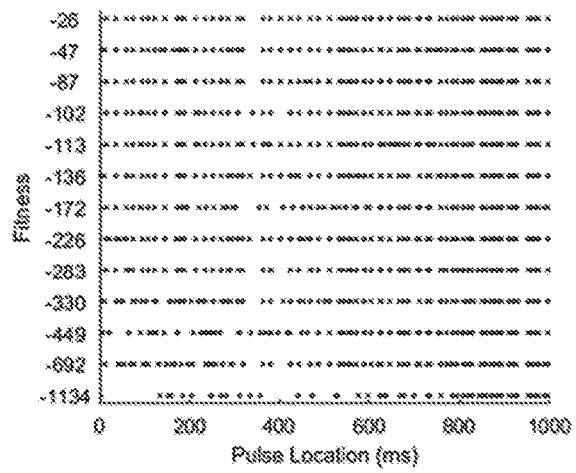 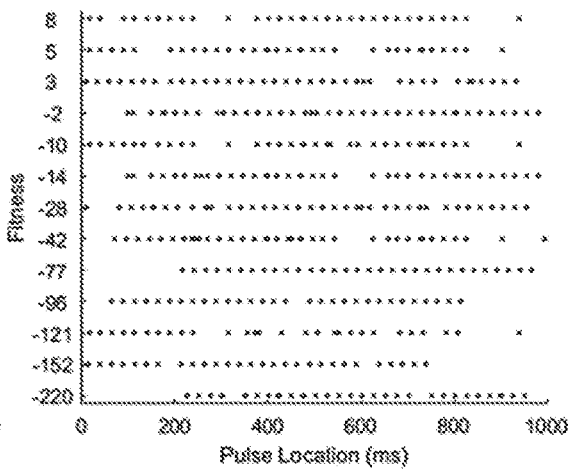
FIG. 27A  FIG. 27B
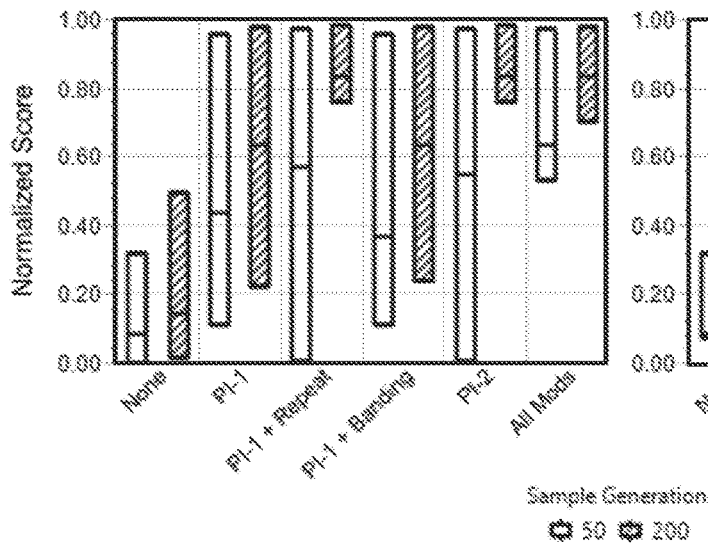 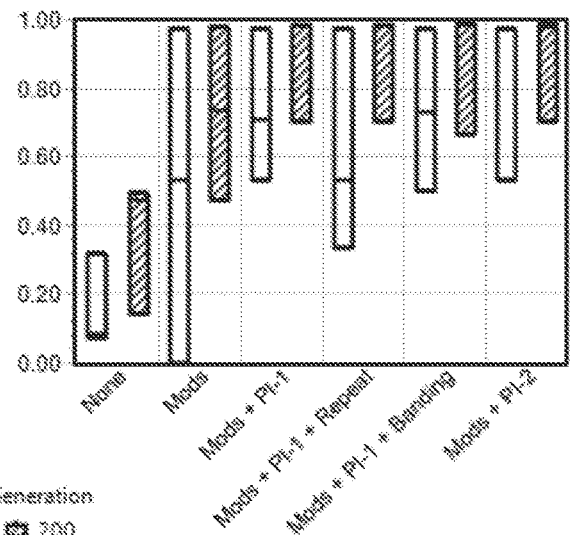
FIG. 28A  FIG. 28B

SYSTEMS AND METHODS FOR DETERMINING OPTIMAL TEMPORAL PATTERNS OF NEURAL STIMULATION

CROSS REFERENCE TO RELATED APPLICATION

This is a 371 national stage patent application, which claims priority to PCT International Patent Application No. PCT/US2017/35556, filed Jun. 1, 2017, and titled SYSTEMS AND METHODS FOR DETERMINING OPTIMAL TEMPORAL PATTERNS OF NEURAL STIMULATION, which claims the benefit of and priority to U.S. Provisional Patent Application No. 62/344,033, filed Jun. 1, 2016 and titled SYSTEM AND METHODS FOR IMPROVED OPTIMAL DESIGN, the disclosures of which are incorporated herein by reference in their entireties.

STATEMENT AS TO FEDERALLY SPONSORED RESEARCH

This invention was made with the support of the United States government under Federal Grant No. NS040894 awarded by the National Institute of Health. The government has certain rights in the invention.

TECHNICAL FIELD

The presently disclosed subject matter relates to temporal patterns of neural stimulation. More particularly, the presently disclosed subject matter relates to the determination of optimal temporal patterns of neural stimulation.

BACKGROUND

A genetic algorithm (GA) is a high dimensional search algorithm that emulates evolutionary biology to find an optimal solution. GAs take advantage of the effects of natural selection, reproduction, migration, and mutation to identify solutions that minimize an associated cost function. GA-based optimization has been successfully applied to a wide variety of problems, including robotic navigation, pattern recognition, speech recognition, and engineering design of circuits.

However, the standard GA method is inadequate in the specific application of designing and selecting temporal patterns of neural stimulation. Although GAs can use real numbers as genes, temporal patterns of stimulation are best implemented in a binary representation where each 1 or 0 corresponds to the presence or absence of a stimulation pulse at each time point. The standard GA performs poorly when applied to temporal patterns of neural stimulation. Therefore, there is a need for improved systems and methods for determining optimal temporal patterns of neural stimulation.

SUMMARY

Disclosed herein are systems and methods for designing optimal temporal patterns of neural stimulation. According to an aspect, a method includes selecting a temporal pattern for neural stimulation. The method also includes determining a mutation type for altering a pattern of pulses of the temporal pattern. The method also includes identifying a location within the pattern of pulses of the temporal pattern to alter based on the determined mutation type. The method further includes altering the pattern of pulses of the temporal pattern based on the identified location and mutation type for application of the altered temporal pattern to a subject.

According to another aspect, a method includes selecting a temporal pattern of neural stimulation as a parent temporal pattern of neural stimulation. The method also includes generating an immigrant temporal pattern of neural stimulation. The method also includes creating a competitive immigrant temporal pattern by crossing the parent temporal pattern with the immigrant temporal pattern. The proportion of the competitive immigrant temporal pattern that comes from the two source patterns varies between generations of the GA. The method further includes inserting the competitive immigrant temporal pattern into a population of competitive temporal patterns.

According to another aspect, a method includes determining one or more features of a temporal pattern of neuronal stimulation associated with a fitness of the temporal pattern. The method also includes storing the one or more features of the temporal pattern associated with the fitness of the temporal pattern. The method also includes generating a predictive temporal pattern of neuronal stimulation including the stored one or more features. The method further includes adding the predictive temporal pattern in a population of temporal patterns of neuronal stimulation.

BRIEF DESCRIPTION OF THE DRAWINGS

The foregoing summary, as well as the following detailed description of various embodiments, is better understood when read in conjunction with the drawings provided herein. For the purposes of illustration, there is shown in the drawings exemplary embodiments; however, the presently disclosed subject matter is not limited to the specific methods and instrumentalities disclosed.

FIG. 12A is an example graphical depiction of an example representation of frequency bias in a point mutation method and a pulse mutation method in accordance with embodiments of the present disclosure;

FIG. 12B is a graphical depiction of an example of an operational difference between the standard point mutation method and the pulse mutation method of the present disclosure in accordance with embodiments of the present disclosure;

FIG. 13 is an graphical depiction of an example method of adding, removing, and moving pulses using the pulse mutation method in accordance with embodiments of the present disclosure;

FIG. 21A is a graphical depiction of an example interpulse interval fit function in accordance with embodiments of the present disclosure;

FIG. 21B is a graphical depiction of an example refractory fit function in accordance with embodiments of the present disclosure;

FIG. 21C is a graphical depiction of an N-Queens fit function in accordance with embodiments of the present disclosure;

FIG. 27A is a raster plot of an example representative subset of stimulation patterns in the final generation of standard genetic algorithm with modifications off in accordance with embodiments of the present disclosure;

FIG. 27B is a raster plot of an example representative subset of stimulation patterns in the final generation of standard genetic algorithm with modifications ON in accordance with embodiments of the present disclosure; and FIGS. 28A and 28B are graphs of example results from combined test functions for each of the four predictive immigrant versions with modifications on and off in accordance with embodiments of the present disclosure.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Articles "a" and "an" are used herein to refer to one or to more than one (i.e. at least one) of the grammatical object of the article. By way of example, "an element" means at least one element and can include more than one element.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Unless otherwise defined, all technical terms used herein have the same meaning as commonly understood by one of ordinary skill in the art to which this disclosure belongs.

Figure 1:
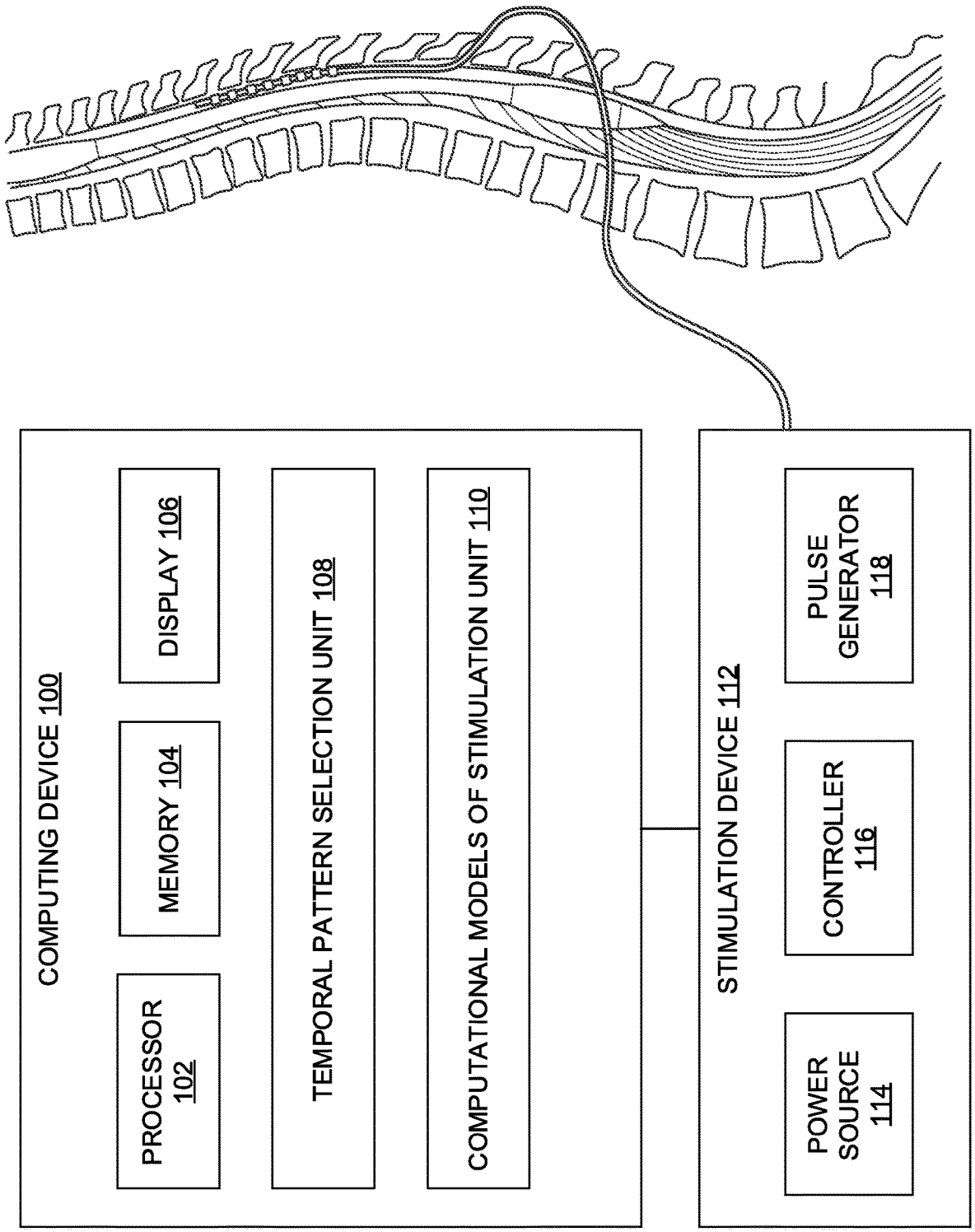
FIG. 1 is a block diagram of an example system for implementing methods of determining optimal temporal patterns of stimulation in accordance with embodiments of the present disclosure.

In accordance with embodiments, disclosed herein are systems and methods for determining optimal temporal patterns of neural stimulation. The system includes a computing device comprising a processor, memory, and a display and configured to execute the temporal design and selection methods in accordance with embodiments of the present disclosure. For example, FIG. 1 illustrates a computing device 100 comprising a processor 102, a memory 104, and a display 106. In accordance with embodiments, the system comprises a temporal pattern selection unit configured to implement the temporal design and selection method in accordance with embodiments of the present disclosure. For example, FIG. 1 illustrates computing device 100 comprising a temporal pattern selection unit 108. In accordance with embodiments, the temporal pattern selection unit comprises one or more modules for performing the methods of the present disclosure.

Figure 2:
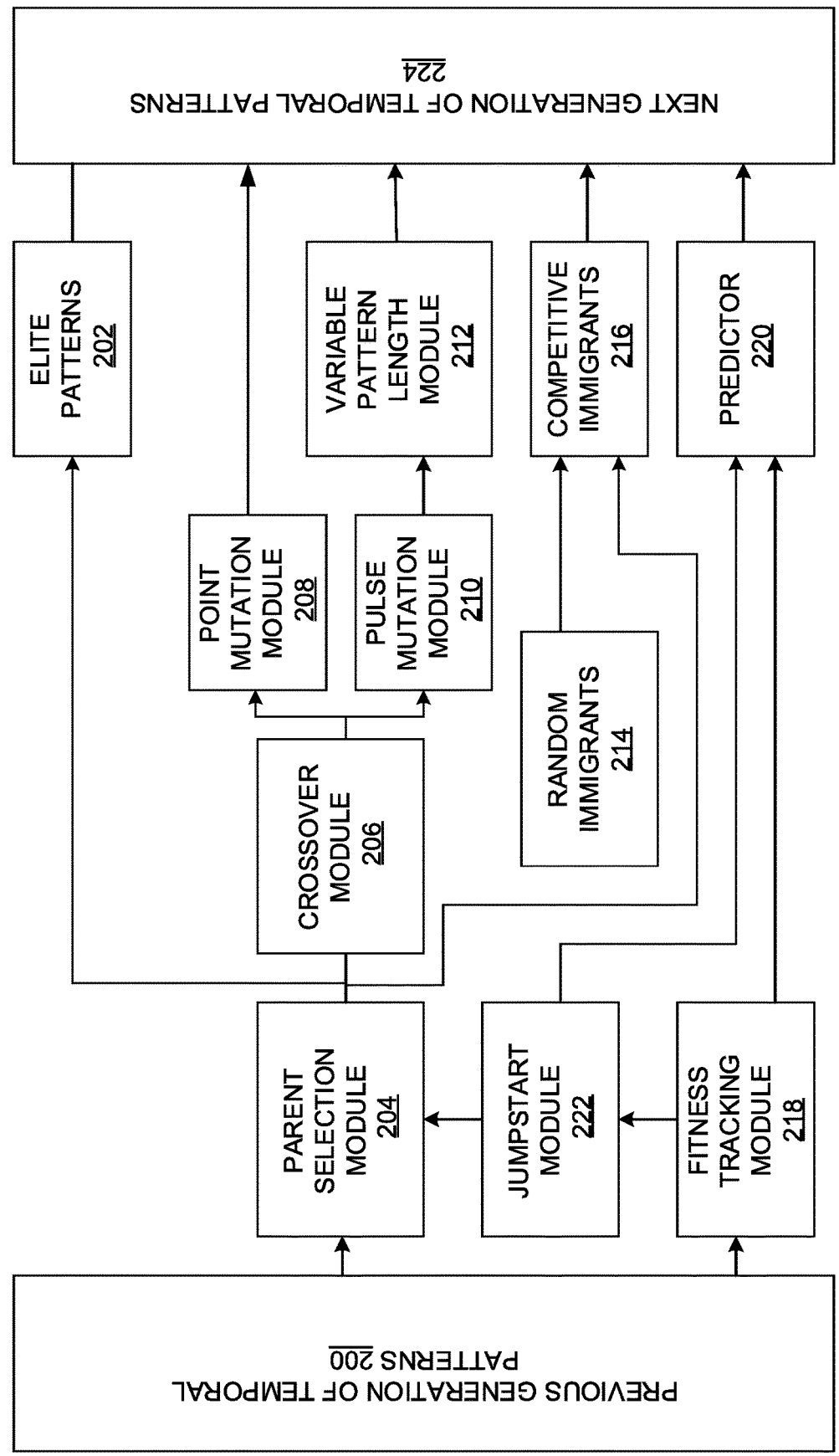
FIG. 2 is a block diagram of an example temporal pattern select unit for implementing methods of determining optimal temporal patterns of stimulation in accordance with embodiments of the present disclosure.
Figure 3:
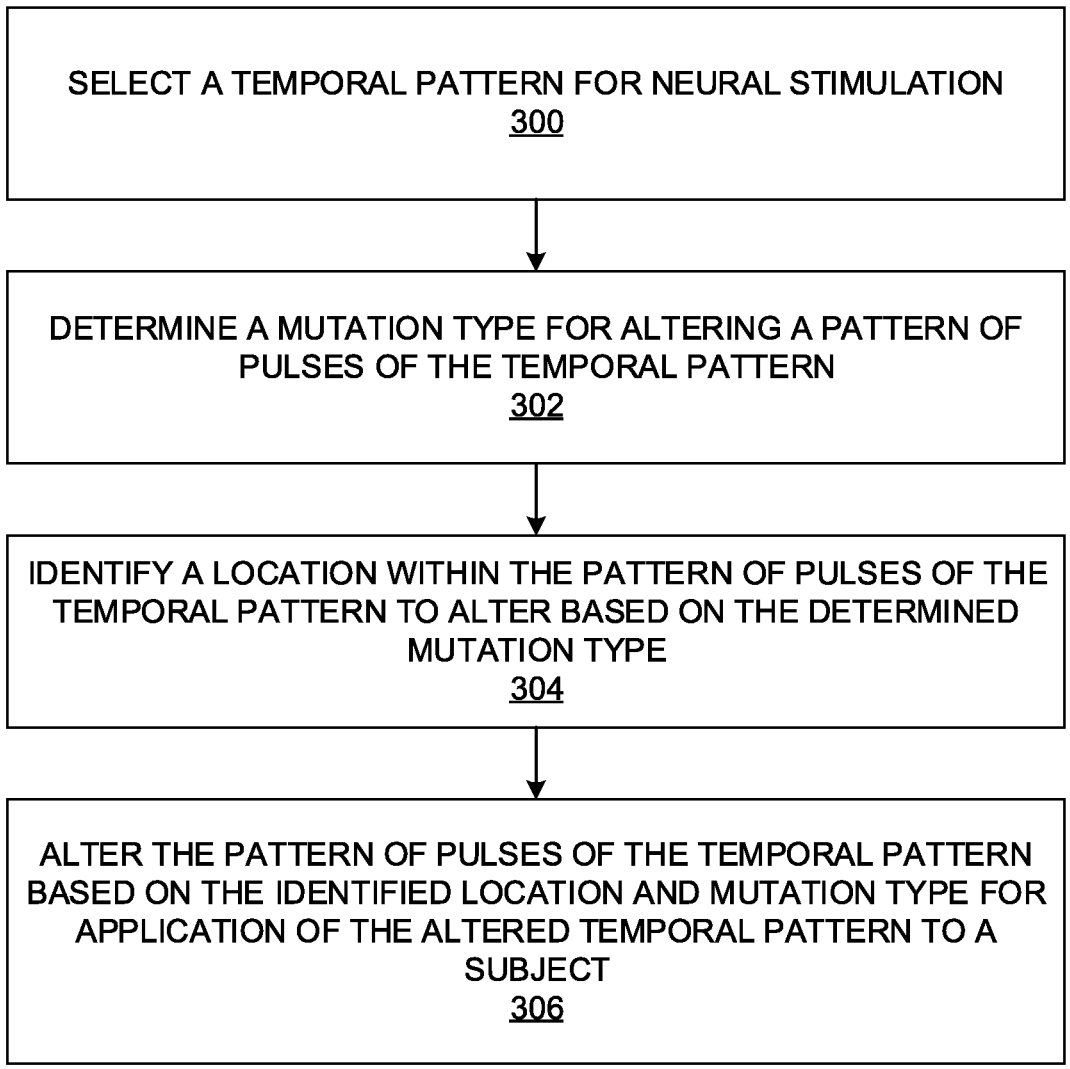
FIG. 3 is a flowchart of an example method for altering a pattern of pulses of a temporal pattern based on an identified location and mutation type for application of the altered temporal pattern to a subject in accordance with embodiments of the present disclosure.

FIG. 2 illustrates temporal selection unit 108 comprising modules 200-224 for performing the methods of the present disclosure. FIG. 3 illustrates a method that includes selecting 300 a temporal pattern for neural stimulation. For example, parent selection module 204 is configured to select a temporal pattern for neural stimulation from a previous generation of temporal patterns 200. In accordance with embodiments, the method may include selecting a pattern of pulses for stimulation of neurons. Also in accordance with embodiments, the method may include selecting a bit train of one or more one bits and zero bits. In this embodiment, a one bit represents a pulse of stimulation, and a zero bit represents a pause in stimulation.

Figure 16A:
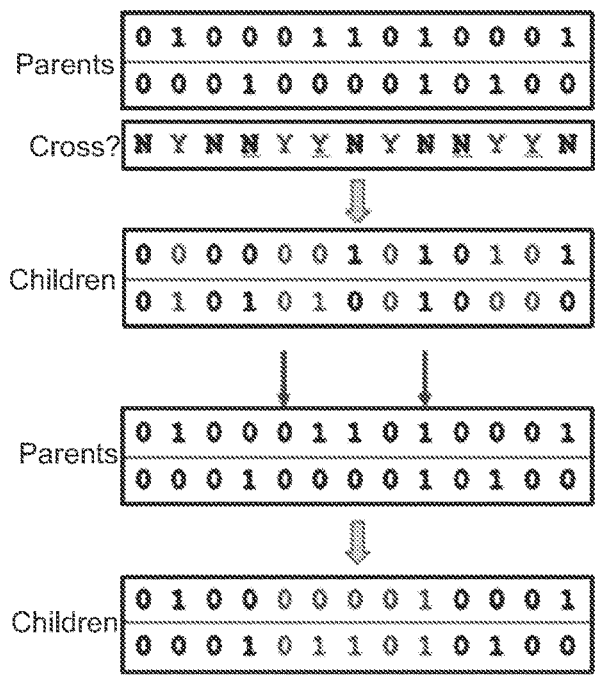
FIG. 16A is a graphical depiction of an example method of crossing bits of temporal patterns in accordance with embodiments of the present disclosure.

Returning to FIG. 2, temporal selection unit 108 comprises a crossover module 206 and point mutation module 208. In this example, crossover module 206 is configured to perform a standard uniform crossover method which randomly determines whether to cross each bit of a temporal pattern with another temporal pattern. Also in this example, crossover module 206 is configured to perform a standard two-point crossover method which randomly selects two points within two temporal patterns and cross the temporal patterns at the selected two points. FIG. 16A illustrates an example of the standard uniform crossover method and the two-point crossover method. In some embodiments, a point mutation module is not utilized. Rather, a pulse mutation module may be used in these instances.

Also in this example, point mutation module 208 is configured to perform a standard point mutation method. This method specifies a set number of mutations, randomly determines the location for each mutation in the gene, and performs a point mutation at each gene location. FIG. 12B illustrates an example temporal pattern mutated using the standard point mutation method.

Returning to FIG. 3, the method includes determining 302 a mutation type for altering a pattern of pulses of the temporal pattern. For example, FIG. 2 illustrates pulse mutation module 210 is configured to determine a mutation type for altering a pattern of pulses of the temporal pattern. In accordance with embodiments, the method also includes determining the mutation type comprises one of adding a pulse to the pattern of pulses and removing a pulse from the pattern of pulses of the temporal pattern. Continuing the example, FIG. 2 illustrates pulse mutation module 210 configured to determine the mutation type comprises one of adding a pulse to the pattern of pulses and removing a pulse from the pattern of pulses of the temporal pattern.

In accordance with embodiments, the method also includes determining the mutation type comprises moving a pulse of the pattern of pulses to another location within the pattern of pulses of the temporal pattern. For example, FIG. 2 illustrates pulse mutation module 210 is configured to determine the mutation type comprises moving a pulse of the pattern of pulses to another location within the pattern of pulses of the temporal pattern.

Returning to FIG. 3, the method includes identifying 304 a location within the pattern of pulses of the temporal pattern to alter based on the determined mutation type. For example, FIG. 2 illustrates pulse mutation module 210 is configured to identify a location within the pattern of pulses of the temporal pattern to alter based on the determined mutation type. In accordance with embodiments, the method also includes randomly identifying a location within the pattern of pulses to alter. Also in accordance with embodiments, the method also includes determining whether the location within the pattern of pulses cannot be altered based on the mutation type. For example, FIG. 2 illustrates pulse mutation module 210 is configured to determine whether the location within the pattern of pulses cannot be alter based on the mutation type. In this embodiment, the method includes selecting a different location within the pattern of pulses to alter based on the mutation type in response to determining that the location within the pattern of pulses cannot be altered. For example, FIG. 2 illustrates pulse mutation module 210 is configured to select a different location within the pattern of pulses to alter based on the mutation type in response to determining that the location within the pattern of pulses cannot be altered.

FIG. 12B shows a graphical depiction of an example implementation of the pulse mutation method in accordance with embodiments. As shown in FIG. 12B, pulse mutation module 210 may determine whether to add a pulse, remove a pulse, or move pulse in the temporal pattern. Also shown in FIG. 12B, locations are selected for implementing the chosen mutation method. FIG. 13 illustrates an example temporal pattern and how it is altered based on the selected mutation method.

In accordance with embodiments, the method may include selecting a predetermined number of locations within the pattern of pulses for altering. For example, FIG. 2 illustrates pulse mutation module 210 is configured to select a predetermined number of locations within the pattern of pulses for altering. For example, FIG. 12B illustrates three locations were selected for altering. However, it should be understood that the three locations selected in FIG. 12B are for illustrative purposes only.

Returning to FIG. 3, the method includes altering 306 the pattern of pulses of the temporal pattern based on the identified location and mutation type for application of the altered temporal pattern to a subject. For example, FIG. 2 illustrates pulse mutation module 210 is configured to alter the pattern of pulses of the temporal pattern based on the identified location and mutation type for application of the altered temporal pattern to a subject. In accordance with embodiments, the method also includes altering the pattern of pulses while maintaining an average frequency of the temporal pattern. This may be achieved by having the same probability of adding, subtracting, or moving a pulse.

The method also includes adding the altered temporal pattern to a population of temporal patterns of a computational model of neural stimulation. For example, FIG. 1 illustrates temporal pattern stimulation unit 108 adds the altered temporal pattern to a population of temporal patterns of computational model of neural stimulation of computational modules of stimulation unit 110. Further discussion regarding computational unit 110 is provided below with regards to FIGS. 22-28.

The method also includes using a neural stimulation device to apply the altered temporal pattern to the subject. FIG. 1 illustrates the system also includes a stimulation device 112 to apply the altered temporal pattern to the subject. FIG. 1 illustrates stimulation device 112 comprises a power source 114, a controller 116, and pulse generator 118. In this example, controller 116 is configured to receive the altered temporal pattern from computing device 100. Continuing the example, pulse generator 118 is configured generate pulses for application to neural network utilizing the altered temporal pattern from controller 116. In this example, pulse generator 118 utilizes power form power source 114 to generate the pulses for application to neural network. The neural network is represented by a spinal column of the subject. However, it should be understood that the spinal column illustrated in FIG. 1 is for illustrative purpose only, and the altered temporal pattern may be applied to any desired neural network.

Figure 4:
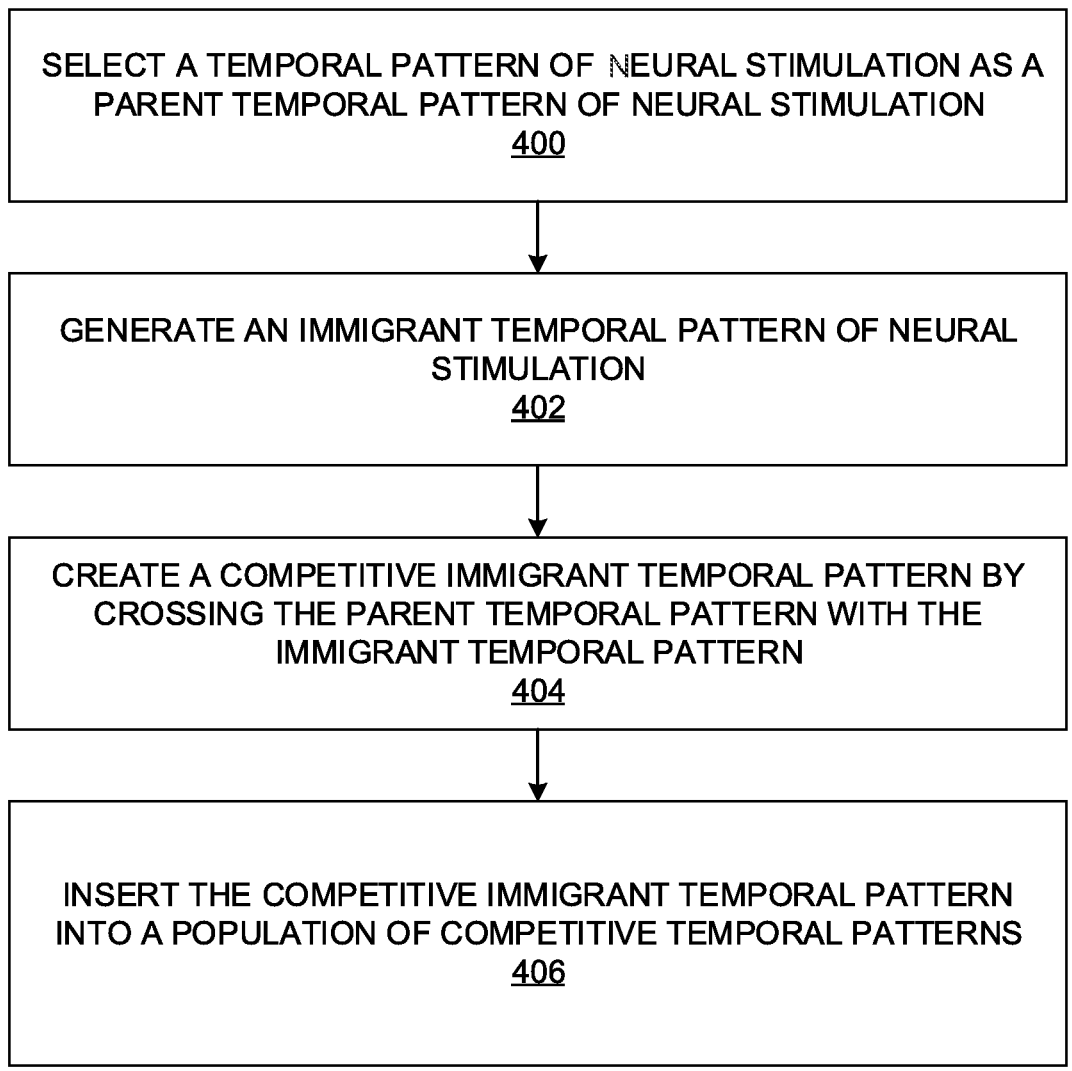
FIG. 4 is a flowchart of an example method inserting a competitive immigrant temporal pattern into a population of competitive temporal patterns in accordance with embodiments of the present disclosure.

According to another aspect, FIG. 4 illustrates a method of selecting 400 a temporal pattern of neural stimulation as a parent temporal pattern of neural stimulation. For example, FIG. 2 illustrates parent selection module 204 is configured to select a temporal pattern of neural stimulation as a parent temporal pattern of neural stimulation. The parent temporal pattern may be determined using a selection method. Examples of potential selection methods may be found in the example of FIGS. 18A and 18B. In accordance with embodiments, the method may include calculating the fitness by utilizing a cost function measuring an efficacy and efficiency of the temporal pattern. FIGS. 19A-19C show an example of one of the test cases (reductions to practice) of the algorithm elements.

Returning to FIG. 4, the method includes generating 402 an immigrant temporal pattern of neural stimulation. For example, FIG. 2 illustrates parent selection module 204 is configured to generate an immigrant temporal pattern of neural stimulation. In accordance with embodiments, the method also includes randomly generating the immigrant temporal pattern from a population of temporal patterns. For example, FIG. 2 illustrates parent selection module 204 is configured to randomly generate the immigrant temporal pattern from a previous generation of temporal patterns 200.

Figure 8:
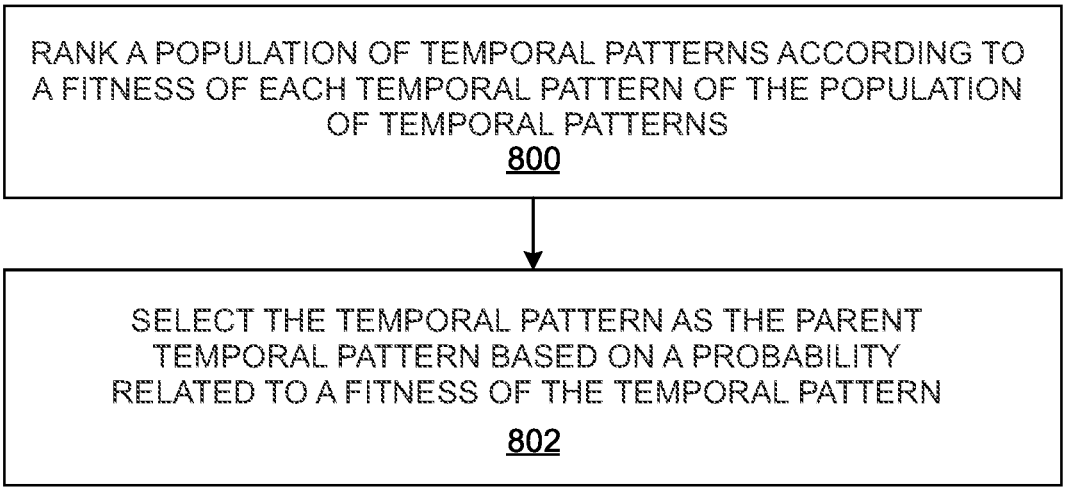
FIG. 8 is a flowchart of an example method of selecting a parent temporal pattern based on a probability related to its fitness

FIG. 8 illustrates the method may include ranking 800 a population of temporal patterns according to a fitness of each temporal pattern of the population of temporal patterns. For example, FIG. 2 illustrates predictor module 220 is configured to determine whether an average associated fitness of a population of temporal patterns with one or more common features meet a predetermined threshold. Returning to FIG. 8, the method may include selecting 802 the temporal pattern as the parent temporal pattern based on a probability related to a fitness of the temporal pattern.

FIG. 4 illustrates the method includes creating 404 a competitive immigrant temporal pattern by crossing the parent temporal pattern with the immigrant temporal pattern. For example, FIG. 2 illustrates competitive immigrants module 216 is configured to create a competitive immigrant temporal pattern by crossing the parent temporal pattern with the immigrant temporal pattern. In accordance with embodiments, the method also includes crossing a bit of the parent temporal pattern with a bit of the immigrant temporal pattern.

Figure 5:
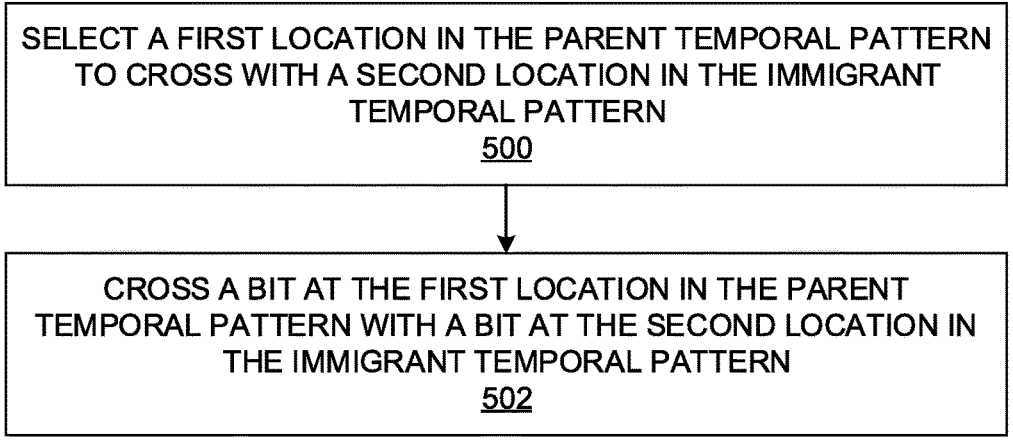
FIG. 5 is a flowchart of an example method of crossing a bit at a first location in the parent temporal pattern with a bit at a second location in the immigrant temporal pattern in accordance with embodiments of the present disclosure.

FIG. 5 illustrates the method may include selecting 500 a first location in the parent temporal pattern to cross with a second location in the immigrant temporal pattern. For example, FIG. 2 illustrates competitive immigrants module 216 is configured to select a first location in the parent temporal pattern to cross with a second location in the immigrant temporal pattern. FIG. 5 also illustrates the method may include crossing 502 a bit from the first location in the parent temporal pattern with a bit at the second location in the immigrant temporal pattern. For example, FIG. 2 illustrates competitive immigrants module 216 is configured to cross a bit from the first location in the parent temporal pattern with a bit at the second location in the immigrant temporal pattern.

Figure 6:
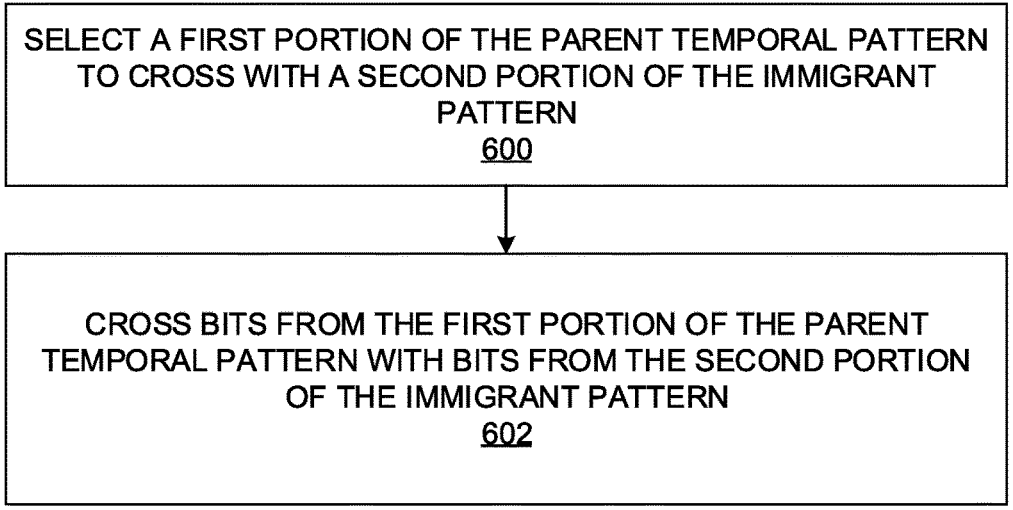
FIG. 6 is a flowchart of an example method of crossing bits from a first portion of the parent temporal pattern with bits from a second portion of the immigrant pattern in accordance with embodiments of the present disclosure.

FIG. 6 illustrates the method may include selecting 600 a first portion of the parent temporal pattern to cross with a second portion of the immigrant pattern. For example, FIG. 2 illustrates competitive immigrants module 216 is configured to select a first portion of the parent temporal pattern to cross with a second portion of the immigrant pattern. FIG.

6 also illustrates the method may include crossing 602 bits from the first portion of the parent temporal pattern with bits from the second portion of the immigrant pattern. For example, FIG. 2 illustrates competitive immigrants module 216 is configured to cross bits from the first portion of the parent temporal pattern with bits from the second portion of the immigrant pattern.

Figure 16B:
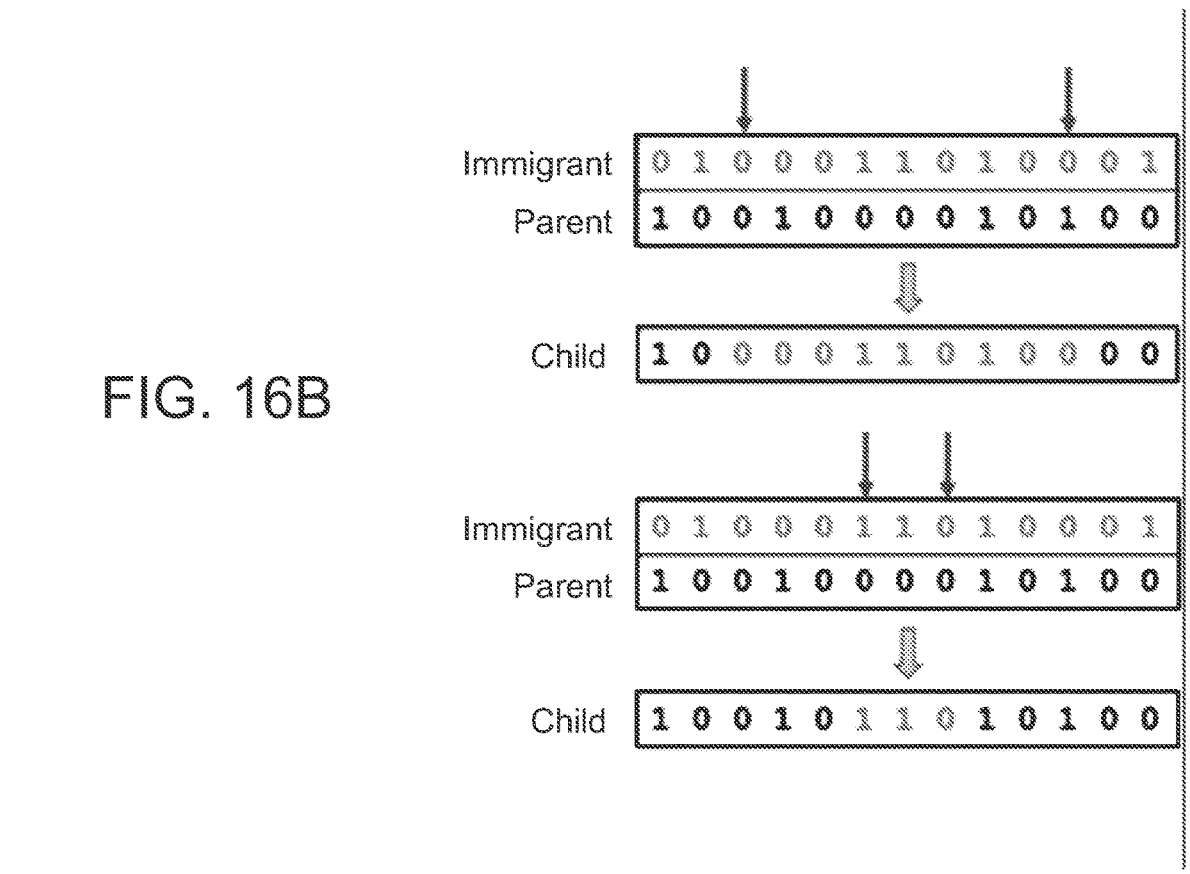
FIG. 16B is a graphical depiction of an example method of crossing a randomly generated immigrant pattern with a parent pattern selected based on fitness in accordance with embodiments of the present disclosure.

The method may include selecting variable lengths of the portion to be crossed across generations. FIG. 16B shows an example immigrant and parent temporal pattern and a method of selecting a first location in the parent temporal pattern to cross with a second location in the immigrant temporal pattern. In this example, the chosen length of the portion to be crossed is different for the two crosses. In both cases, once the length of the portion to be crossed is chosen, a starting location is randomly determined. The portion to be crossed is then designated as that which starts at that starting location and continues for the determined portion length. This region is then crossed between the immigrant and parent temporal patterns.

Figure 17B:
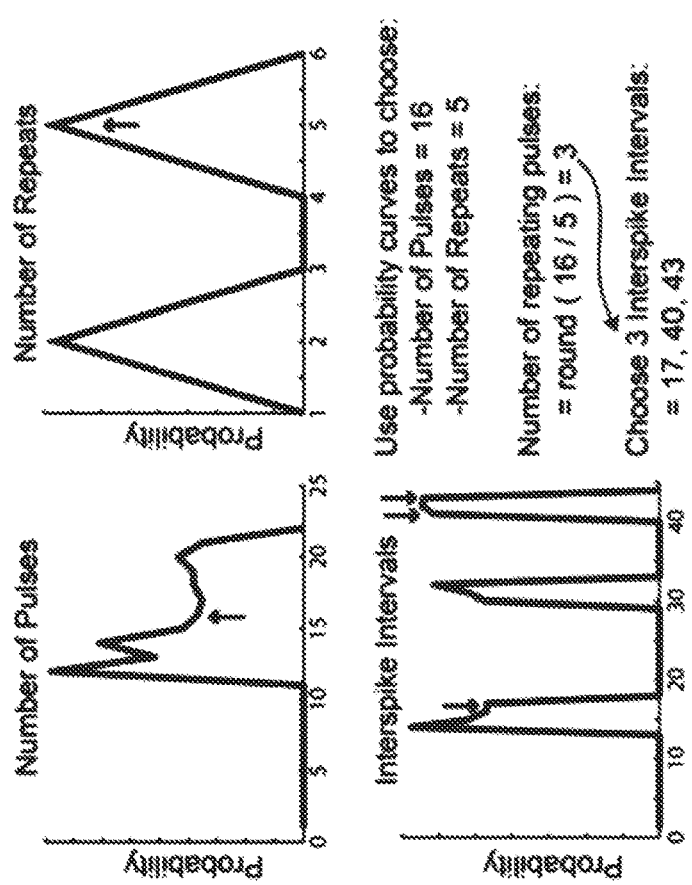
FIG. 17B is a graphical depiction of an example method of interpulse interval creation using a repeats method in accordance with embodiments of the present disclosure.
Figure 17A:
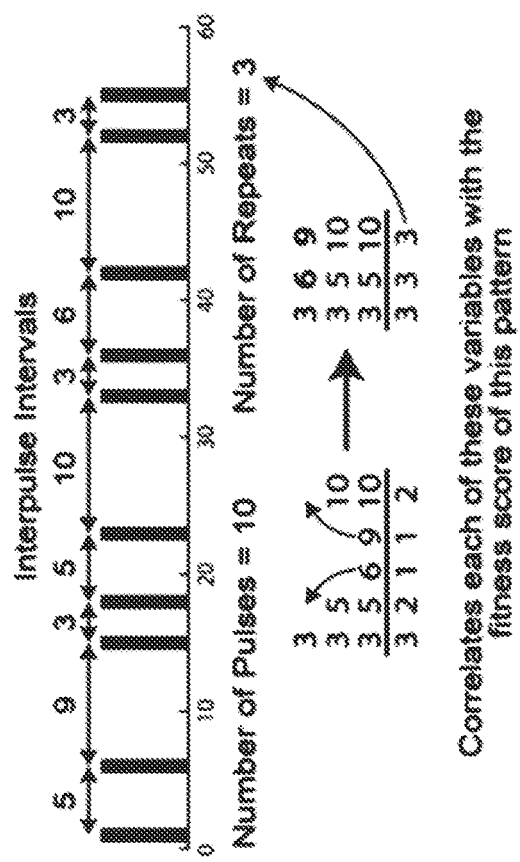
FIG. 17A is a graphical depiction of an example method for the performance tracking state of a predictive immigrant function in accordance with embodiments of the present disclosure.

According to another aspect, a method includes determining 700 one or more features of a temporal pattern of neuronal stimulation associated with a fitness of the temporal pattern. For example, FIG. 2 illustrates fitness tracking module 218 is configured to determine one or more features of a temporal pattern of neuronal stimulation associated with a fitness of the temporal pattern. In accordance with embodiments, the method may include determining one of interpulse intervals, a number of pulses, and a number of interpulse interval subpatterns within the temporal pattern. FIG. 17A shows a graphical depiction of an example of determining one of interpulse intervals, a number of pulses, and a number of interpulse interval subpatterns within the temporal pattern.

Figure 9:
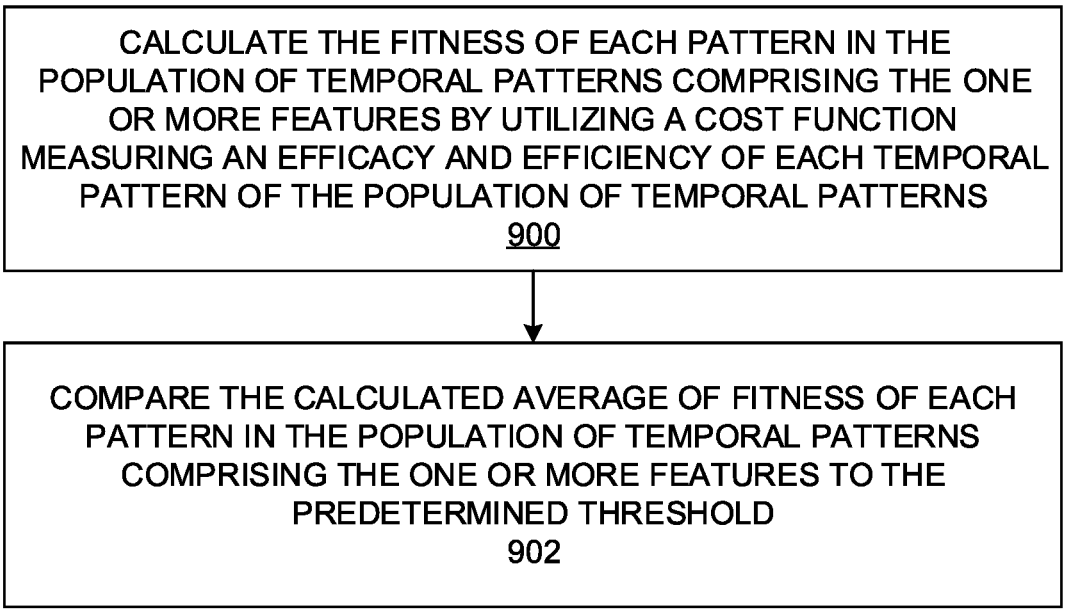
FIG. 9 is a flowchart of an example method of comparing a calculated average of fitness of each pattern in the population of temporal patterns comprising one or more features to a predetermined threshold in accordance with embodiments of the present disclosure.

FIG. 9 illustrates the method may include calculating 900 the fitness of each pattern in the population of temporal patterns comprising the one or more features by utilizing a cost function measuring an efficacy and efficiency of each temporal pattern of the population of temporal patterns. For example, FIG. 2 illustrates predictor module 220 is configured to calculate the fitness of each pattern in the population of temporal patterns comprising the one or more features by utilizing a cost function measuring an efficacy and efficiency of each temporal pattern of the population of temporal patterns. Returning to FIG. 9, the method may include comparing 902 the calculated average associated fitness of each pattern in the population of temporal patterns comprising the one or more features to the predetermined threshold.

Figure 7:
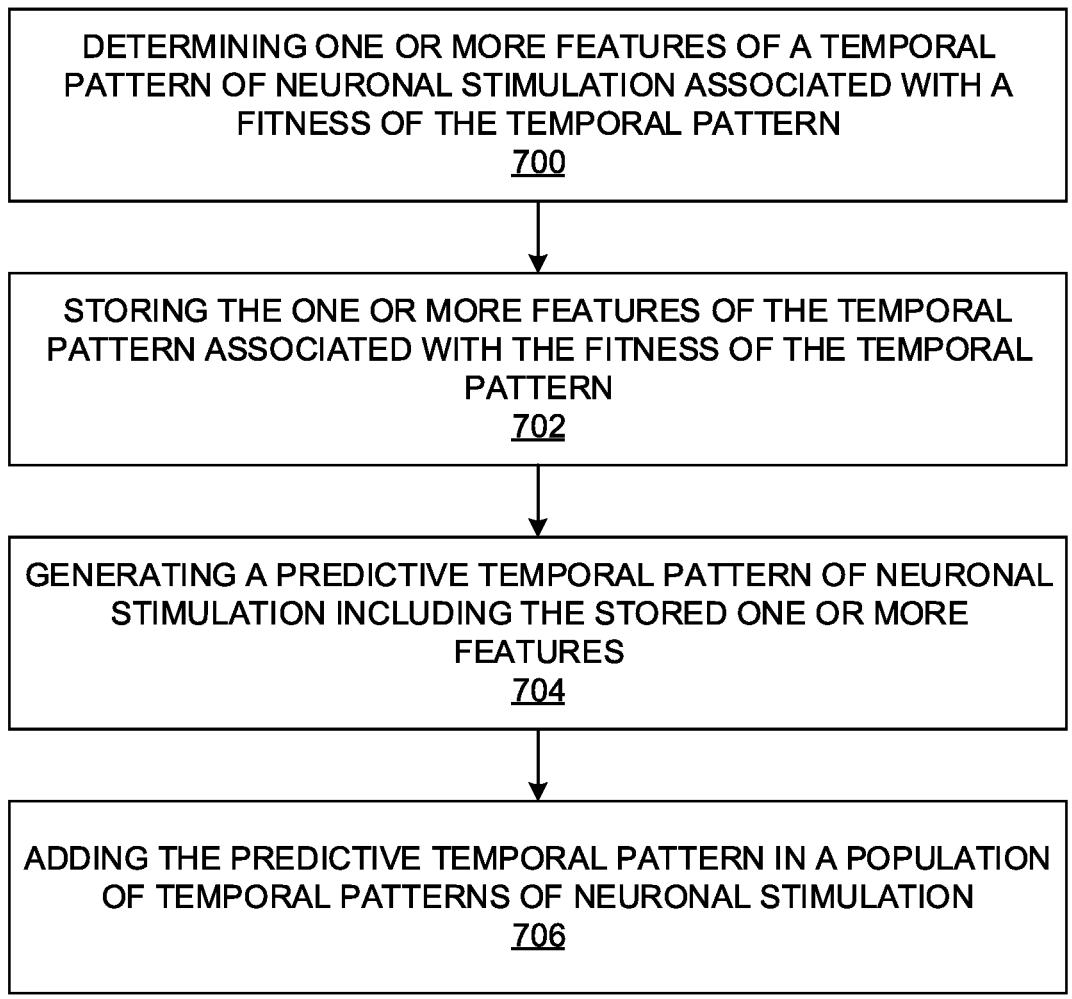
FIG. 7 is a flowchart of an example method of adding a predictive temporal pattern in a population of temporal patterns of neuronal stimulation in accordance with embodiments of the present disclosure.

Returning to FIG. 7, the method includes storing 702 the one or more features of the temporal pattern associated with the fitness of the temporal pattern. For example, FIG. 2 illustrates predictor module 220 is configured to store the one or more features of the temporal pattern associated with the fitness of the temporal pattern. FIG. 7 also illustrates the method includes generating 704 a predictive temporal pattern of neuronal stimulation including the stored one or more features. For example, FIG. 2 illustrates predictor module 220 is configured to generate a predictive temporal pattern of neuronal stimulation including the stored one or more features.

Figure 10:
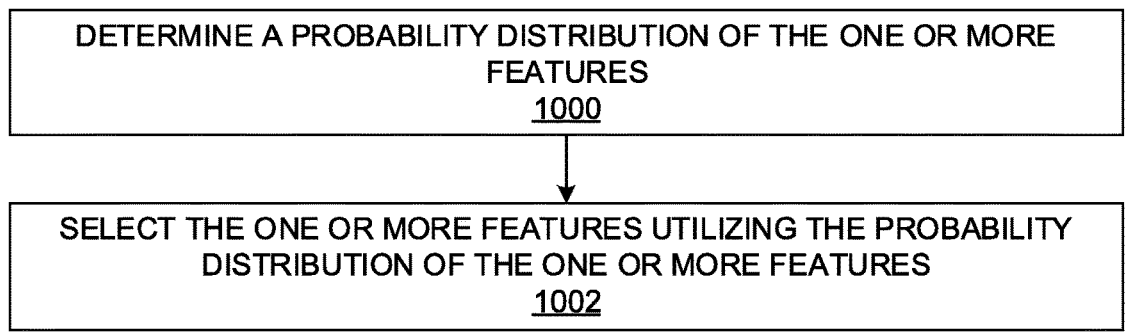
FIG. 10 is a flowchart of an example method of selecting one or more features utilizing a probability distribution of the one or more features in accordance with embodiments of the present disclosure.

FIG. 10 illustrates the method may include determining 1000 a probability distribution of the one or more features. For example, FIG. 2 illustrates predictor module 220 is configured to determine a probability distribution of the one or more features. FIG. 17B shows a graphical depiction an example of determined probability distributions of one or more features of a temporal pattern. Returning to FIG. 10, the method may include selecting 1002 the one or more features utilizing the probability distribution of the one or more features. For example, FIG. 2 illustrates predictor module 220 is configured to select the one or more features utilizing the probability distribution of the one or more features. FIG. 17B also shows a graphical depiction an example of selecting the one or more features utilizing the probability distribution of the one or more features.

In accordance with embodiments, the method may include determining a probability distribution of a number of pulses and interpulse intervals of the temporal pattern. Also in accordance with embodiments, the method may include determining a number of repeating interpulse interval subpatterns of the temporal pattern. In this embodiment, the method may also include determining a probability of distribution of the number of repeating interpulse interval subpatterns of the temporal pattern.

Figure 11A:
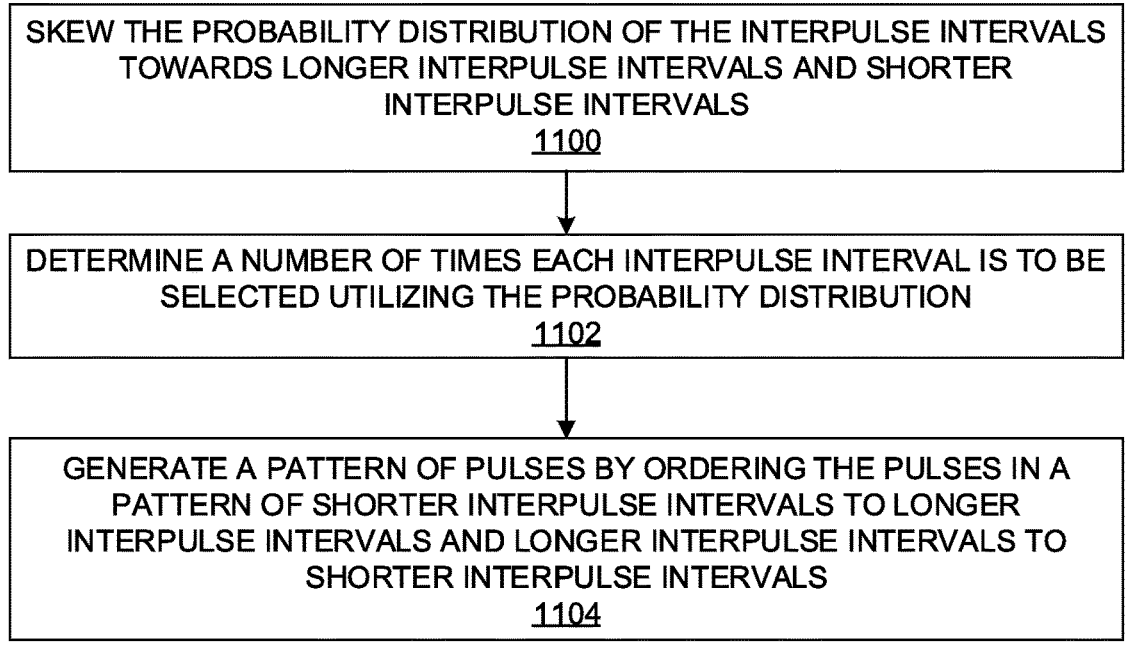
FIG. 11A is a flowchart of an example method of generating a pattern of pulses by ordering the pulses in a pattern of shorter interpulse intervals to longer interpulse intervals and longer interpulse intervals to shorter interpulse intervals in accordance with embodiments of the present disclosure.

In accordance with embodiments, the method may include determining a probability distribution of interpulse intervals of the temporal pattern. FIG. 11A illustrates the method may include skewing 1100 the probability distribution of the interpulse intervals towards longer interpulse intervals and shorter interpulse intervals. For example, FIG. 2 illustrates predictor module 220 is configured to skew the probability distribution of the interpulse intervals towards longer interpulse intervals and shorter interpulse intervals. FIG. 11A also illustrates the method may include determining 1102 a number of times each interpulse interval is to be selected utilizing the skewed probability distribution. For example, FIG. 2 illustrates predictor module 220 is configured to determine a number of times each interpulse interval is to be selected utilizing the skewed probability distribution. Returning to FIG. 11A, the method may include generating 1104 a pattern of pulses by ordering the pulses in a pattern of shorter interpulse intervals to longer interpulse intervals and longer interpulse intervals to shorter interpulse intervals. For example, FIG. 2 illustrates predictor module 220 is configured to generate a pattern of pulses by ordering the pulses in a pattern of shorter interpulse intervals to longer interpulse intervals and longer interpulse intervals to shorter.

Returning to FIG. 7, the method includes adding 706 the predictive temporal pattern in a population of temporal patterns of neuronal stimulation. For example, FIG. 2 illustrates predictor module 220 is configured to add the predictive temporal pattern in a population of temporal patterns, such as next generation of temporal patterns 224.

Figure 11B:
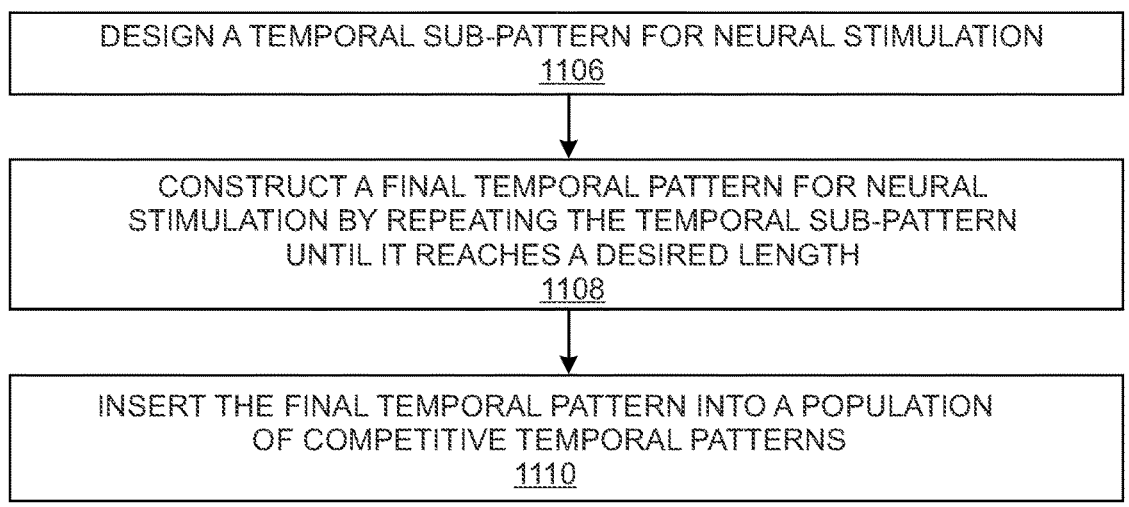
FIG. 11B is a flowchart of an example method of variable pattern length modification in accordance with embodiments of the present disclosure.

FIG. 11B illustrates a flowchart of an example method of variable pattern length modification in accordance with embodiments of the present disclosure. Referring to FIG. 11B, the method may include designing 1106 a temporal sub-pattern for neural stimulation. The length of the temporal sub-pattern may vary across generations. The method also includes constructing 1108 a final temporal pattern for neural stimulation by repeating the temporal sub-pattern until it reaches a desired length. The final temporal pattern may be constructed by either directly repeating the sub-pattern or by repeating the interpulse intervals of the sub-pattern. Further, the method of FIG. 11B includes inserting 1110 the final temporal pattern into a population of competitive temporal patterns.

It is noted that neuromodulation via electrical stimulation can be used for cochlear stimulation to restore hearing, retinal stimulation to restore sight, sacral nerve stimulation to restore bladder function, deep brain stimulation for Parkinson's disease, spinal cord stimulation for pain, and many other applications. Neuromodulation devices typically deliver stimulation pulse trains with regular, repeating interpulse intervals and only the frequency, pulse duration, and amplitude are varied. However, non-regular temporal patterns of stimulation may be more effective, more efficient, more versatile, and produce fewer side effects. For parameters such as pulse width and amplitude, there are well understood relationships between the parameter and the effect, e.g. increasing the amplitude increases neural activation. However, there is no clear basis for selection of temporal patterns of stimulation, which requires either ad hoc selection or rigorous model-based design and evaluation. Stimulation parameters have been optimized using genetic algorithms, particle swarm optimization, and artificial neural networks. Application-specific modifications to the optimization methodology can improve performance, and significant effort has been made in other fields to identify the best algorithm and modifications. Disclosed herein in accordance with embodiments of the present disclosure are systems and methods for improving the convergence speed and accuracy of a genetic algorithm for model-based design of optimized temporal patterns of stimulation.

GA is a parameter optimization technique inspired by biological evolution that uses the concepts of mating, random mutation, genetic diversity, and natural selection. A GA is most easily described using metaphors from evolution, starting with a group of input vectors called "organisms" that contain independently manipulated components called "genes" which represent modifiable parameters to be optimized by the algorithm. In addition, the GA uses a cost function to determine the performance or "fitness" of each organism in the "population", and then uses a method of "natural selection" to assign each organism a probability of "mating" proportional to its fitness. During mating, the genes of the two organisms are combined by "cross-over" and "mutation" to form a "child" organism. These children are joined by "immigrants", new organisms with random genetic information, to create the next generation of the population, and the process is repeated. In addition, "elite" organisms with the highest fitness are typically passed onto the next generation with no modification. This combination of mating, mutation, immigration, and preservation of elites is collectively referred to as repopulation. The GA performs repopulation and scoring iteratively to search the parameter space and thereby arrive at an optimal solution.

Although GAs can use real numbers as genes, temporal patterns of stimulation are best implemented in a binary representation where each 1 or 0 corresponds to the presence or absence of a stimulation pulse at each time point. Although binary repopulation techniques of parent selection, cross-over, and mutation can be highly standardized, the performance of this standard GA was surprisingly poor. This motivated our effort to improve GA performance by incorporating principles specific to the design of temporal patterns of stimulation. In accordance with embodiments, five modifications to the standard repopulation method are provided, as shown in FIG. 2, and evaluate their utility on three test functions and two biophysically-based computational models of neural stimulation. The results were compared to the performance of a standard GA designed with established binary repopulation techniques.

Point mutations and probabilistic mutations are two example methods for performing mutations on a binary GA. Point mutations are performed by specifying a set number of mutations and then randomly determining the location within the gene for each mutation. Probabilistic mutations can be performed by using a probability to determine whether a mutation may occur at each point in the gene; this allows for a variable number of mutations. In both cases, the actual mutation is performed by simply switching the value from a one to a zero, or vice versa.

Both approaches can bias solution towards an equal proportion of ones and zeros, as shown in FIG. 12A. Though they may be useful when this proportion holds no significance, in our application it alters the average pulse repetition frequency of stimulation pulse trains. Relevant temporal patterns of stimulation tend to be characterized by infrequent pulses and relatively long periods without pulses. For example, a standard 100 Hz stimulation pattern with a temporal resolution of 1 ms has a 9:1 ratio of zeros to ones, and using either of the standard mutation methods may result in a bias towards higher frequencies. In examples disclosed herein, the standard mutation methods were modified to solve this problem.

A pulse mutation method (PMM, FIG. 12B) uses a preset number of mutations, in this case 0.5% of the length of the pattern, to prevent frequency bias. The PMM randomly chooses whether to add a pulse, remove a pulse, or move a pulse and then randomly chooses the location in the gene to mutate. If the destination in the gene for the moved pulse already contains a pulse, then a different pulse is chosen to move. This method introduces no pulse repetition frequency bias as there is an equal probability of increasing or decreasing the number of pulses.

FIG. 12A illustrates representation of frequency bias in the two mutation methods. Random patterns were initialized with a total length of 200 and either 25 or 175 pulses. Each pattern was then mutated 200 times using either the standard point mutation or PMM. FIG. 12B illustrates comparison of the standard point mutation and PMM. In one method, pulses locations are randomly chosen, and the values at those locations are changed. In the PMM, the mutation type is first randomly determined, then the locations are determined, and finally the mutation is performed.

FIG. 13 illustrates examples of one of adding, removing, and moving a pulse in a temporal pattern, or gene, in accordance with embodiments of the present disclosure. In accordance with embodiments, the method may include determining one or more locations of gaps and pulses within the temporal pattern. The method may also include one of adding, removing, and moving a pulse in the temporal pattern based on the determined one or more locations of gaps and pulses within the temporal pattern. In accordance with embodiments, new pulses are added, removed, or moved in the temporal pattern, or gene, with equal probability.

Figure 14:
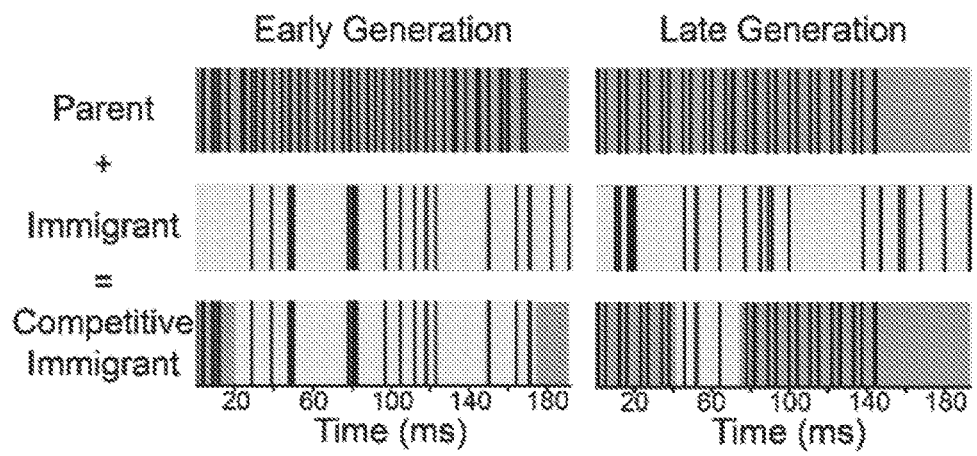
FIG. 14 is a graphical depiction of a method of creating of competitive immigrant temporal patterns in accordance with embodiments of the present disclosure.

Randomly generated organisms—termed immigrants or invaders—are a common feature of GAs to maintain genetic diversity in the population. However, these random immigrants may rarely be selected to reproduce as the average fitness of the population quickly exceeds that of the randomly-generated immigrants, and their selection probability becomes negligible. Some parent selection methods force mating with immigrants, but the resulting children still underperform their peers. Therefore, the immigrant method may be modified in accordance with embodiments to produce immigrants whose fitness remained competitive across the generations of the GA. Competitive immigrants (CI), as illustrated in FIG. 14, may be created by mating a random immigrant with a parent chosen from the population via the standard parent selection method. This produced an organism with a portion of its gene from the high-fitness parent and the remainder from the randomly generated immigrant. To maintain comparable fitness between immigrants and the population, the portion of the competitive immigrant genome that was from the parent increased over generations: the competitive immigrants were completely random until generation 5 and then the proportion of random genetic contribution declined progressively to 2.5% at generation 200.

FIG. 14 illustrates a method for creation of CI in accordance with embodiments of the present disclosure. A parent is selected based on its fitness and a random immigrant is created. The parent and immigrant are then crossed to produce the CI that is inserted into the population. The proportion of the CI from the parent increases over subsequent generations. Dark regions in the CI come from the parent, and light regions come from the immigrant.

Figure 15A:
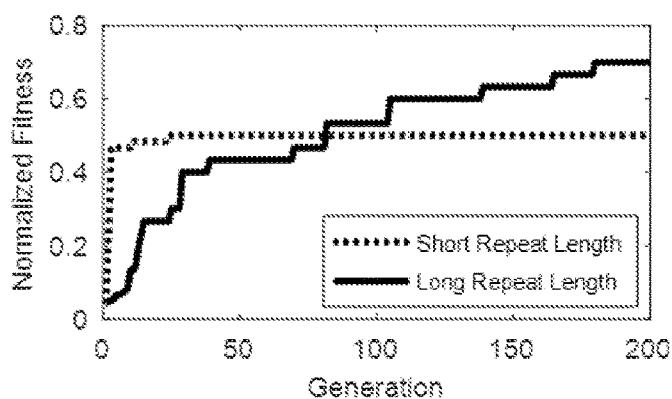
FIG. 15A is a graphical depiction of example fitness levels achieved by a GA using a full-size repeat length and a significantly smaller repeat length in accordance with embodiments of the present disclosure.
Figure 15B:
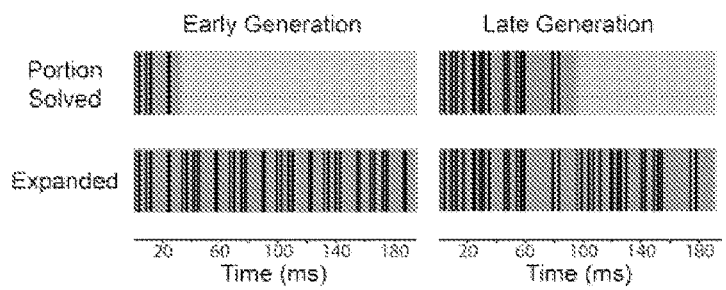
FIG. 15B is a graphical depiction of example results from a method of variable pattern length modification in accordance with embodiments of the present disclosure.
Figure 15C:
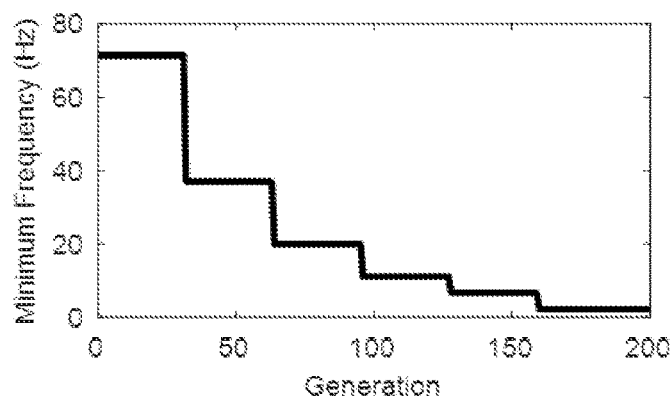
FIG. 15C is a graphical depiction of an example of a minimum frequency content possible in each generation using the variable pattern length modification in accordance with embodiments of the present disclosure.

Since therapeutic electrical stimulation is typically applied from minutes to days, the GA is designed to solve for a pattern of limited length that is then repeated for the duration of stimulation. Choosing a shorter pattern length tends to increase the speed of convergence of the algorithm, but may preclude potentially important low frequency variation, as illustrated in FIG. 15A. The variable pattern length (VPL) modification progressively increases the length of the stimulation pattern across generations, as illustrated in FIG. 15B. Early patterns are created from subsegments of the pattern length, which are replicated and concatenated to produce full length patterns. The proportion of each organism that is used in this process increases over the course of several generations until the GA manipulates the full-length pattern, as illustrated in FIG. 15C.

FIG. 15A illustrates the fitness levels achieved by a GA using the full-size repeat length and a significantly smaller repeat length. FIG. 15B illustrates a method for the variable pattern length modification in accordance with embodiments of the present disclosure. In early generations, only a small portion of the pattern is solved with the GA, and is then duplicated to fill out the full length of the pattern. Over subsequent generations, the portion of the pattern that the GA solves is increased, until it solves for the entire pattern length. FIG. 15C illustrates the minimum frequency content (Hz) possible in each generation using the VPL method for a 450 bit long pattern. As the pattern length increases across generations, the minimum frequency content decreases.

FIG. 16A illustrates a uniform crossover method and a two-point crossover method for producing new temporal patterns, or genes. In the uniform crossover method, a random determination is made to determine if there will a cross for each bit of the temporal pattern, or gene. In the crossover method, a random selection of two points within the temporal pattern, or gene, is made and the two parents are crossed at those two locations.

FIG. 16B illustrates an example of a method for creation of Competitive Immigrants in accordance with embodiments of the present disclosure. In accordance with embodiments, immigrant temporal patterns are first randomly generated. A parent is then selected based of a fitness associated with that pattern, in accordance with embodiments. As shown in FIG. 16B, the immigrant temporal pattern and the parent temporal pattern are then crossed to create a child that is inserted into the population of temporal patterns. The proportion of the child that is from the immigrant decreases over time. This allows the immigrants to remain competitive throughout generations of temporal patterns.

GAs evaluate every pattern of every generation, but typically only use information from the most recent generation to populate the next. This results in substantial information being discarded. To take advantage of the performance sampling that occurs for all patterns in each generation, predictive immigrants (PI) may be used that incorporate the attributes of the highest scoring patterns across generations. The PI function tracks the features of patterns that score highest in each generation, creates new patterns that incorporate these features, and replaces half of the immigrants with these patterns. The PI function has two major components: performance tracking and pattern creation. In the tracking stage, as illustrated in FIG. 17A, it records for each pattern the number of pulses, the interpulse intervals (IPIs), and the number of repeating IPI subpatterns ($N_r$). Subpatterns are determined using the following procedure:

1. Determine how many repeats of each individual IPI are in a pattern: $n_r$.
2. For IPIs with $n_r$ less than 10% of the total number of IPIs in a pattern:
   a. If a neighboring IPI has an $n_r$ greater than 10%, then add the $n_r$ to it
   b. If there is not, then ignore this WI
3. For the remaining IPIs, take the lowest $n_r$, this is the number of repeating IPI subpatterns: $N_r$.

These features may subsequently be associated with the pattern's fitness and added to a collective table that contains the data from every pattern tested. This table is then used to create probability distributions for choosing each pattern feature, with the probability of choosing a given value for a feature proportional to the fitness of that feature averaged across generations.

FIG. 17A illustrates a method for the performance tracking stage of the predictive immigrant (PI) function. Three features are tracked: the interpulse intervals, the number of pulses, and the number of repeats, and each feature is associated with the fitness of the pattern. FIG. 17B illustrates an IPI pattern creation using the Repeats method. Probability density curves for the three tracked features (interpulse intervals, number of pulses, and number of repeats) are used to produce new patterns.

The PI function may use three different methods to create patterns from these data, each producing patterns with different desired attributes. The first is an example method, which only uses the number of pulses and the IPIs:

1. Use the probability distribution of the number of pulses to choose a number of pulses: $N_p$
2. Use the probability distribution of the IPIs to choose $N_p-1$ IPIs
3. Create a pattern with the corresponding IPIs in random order
4. If the pattern is longer than the desired overall pattern length, truncate it to length The second is the Repeats method, illustrated in FIG. 17B, which chooses fewer IPIs that are repeated $N_r$ times, and was inspired by observing that many optimal patterns exhibited a repeating subpattern of IPIs:

1. Use the probability distribution of the number of pulses to choose a number of pulses: $N_p$
2. Use the probability distribution of the number of repeats to choose $N_r$
3. Use the probability distribution of the IPIs to choose $(N_p-1)/N_r$ IPIs
4. Create a subpattern with the chosen IPIs and repeat it $N_r$ times
5. If the pattern is longer than the desired overall pattern length, truncate it The third technique is the Banding method and may be based on observations that the optimal pattern often appeared to be semi-regular (e.g., a bursting pattern), and that persistent sub-optimal solutions (local maxima) were patterns where the longest IPIs (e.g., interburst intervals) were incorrect:

1. Skew the probability distribution of IPIs towards higher or lower values
2. Use the skewed IPI distribution to determine the number of times each IPI will be used
3. Create a pattern by placing pulses with given IPI's from smallest to largest and then largest to smallest 4. Repeat this process until the pattern exceeds the desired length and truncate Four versions of the PI were tested: Original (PI-1), Repeats, Banding, and a combination of Repeats and Banding (PI-2). Repeats and Banding alone were comparable to PI-1 when averaged across the test functions, but the combination of the two substantially increased performance. PI-2 was the most effective of the PI variations and was used for all subsequent evaluations reported herein. The results comparing the different PI versions are disclosed herein.

Figure 18A:
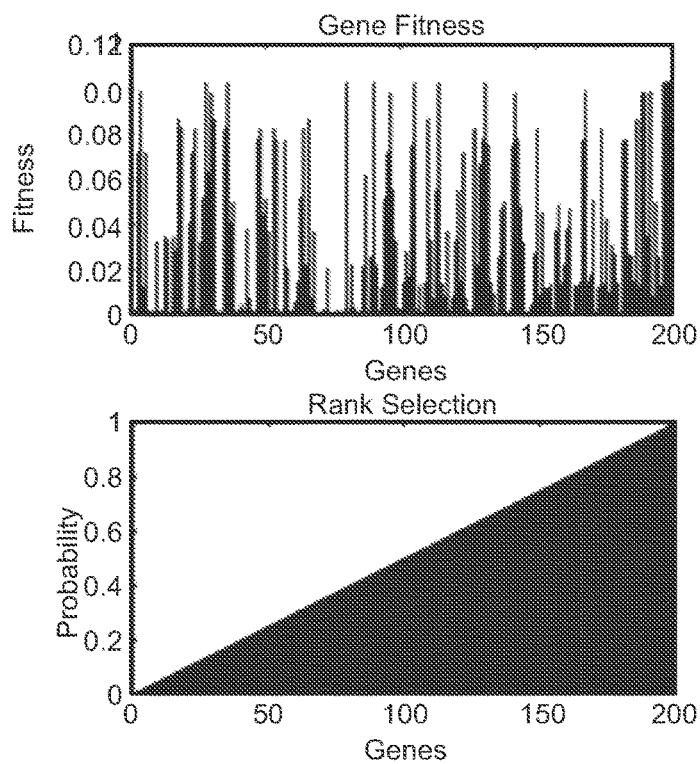
FIG. 18A is a graphical depiction of fitness across a population of temporal patterns and an example probability distribution applied when performing rank selection of parent temporal patterns in accordance with embodiments of the present disclosure.
Figure 18B:
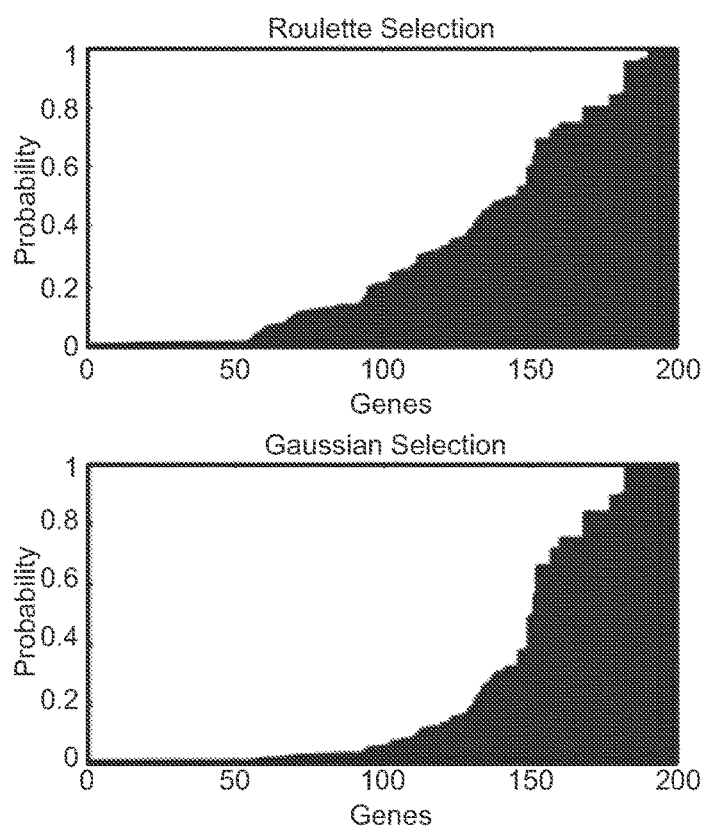
FIG. 18B is a graphical depiction of example probability distributions applied during roulette selection and Gaussian selection of parent temporal patterns in accordance with embodiments of the present disclosure.
Figures 19A, 19B, 19C:
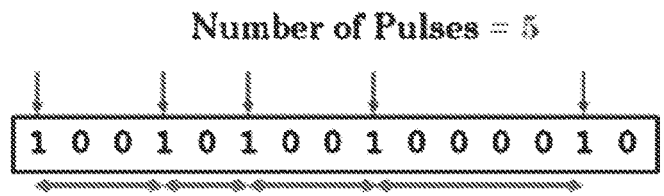
FIG. 19A is a graphical depiction of an example temporal pattern and a calculation of a number of pulses and interspike intervals of the temporal pattern in accordance with embodiments of the present disclosure.
FIG. 19B is a graphical depiction of an example method of associating a fitness with spike count for each temporal pattern in a population of temporal patterns and storing the feature data in accordance with embodiments of the present disclosure.
FIG. 19C is a graphical depiction of an example method of associating a fitness with the interpulse intervals for a given pattern in a population of temporal patterns and storing the feature data in accordance with embodiments of the present disclosure.

FIG. 18A illustrates a graphical depiction of fitness across a population of temporal patterns and an example probability distribution applied when performing rank selection of parent temporal patterns in accordance with embodiments of the present disclosure. Parent temporal patterns are selected in direct proportion to their rank in the rank selection method. FIG. 18B illustrates a graphical depiction of a roulette selection method of temporal patterns that also selects the temporal patterns in direct proportion to their rank. FIG. 18B illustrates a graphical depiction of a Gaussian selection method in accordance with embodiments of the present disclosure. In embodiments, the fitness of the temporal patterns, or genes, are fit to a normal Gaussian distribution. In accordance with embodiments, the Gaussian selection method includes selecting the parent temporal patterns in proportion to their new normalized fitness.

FIGS. 19A-19C illustrates an example of tracking and determining an average fitness of a population of temporal patterns based on an optimal number of spikes (e.g. pulses) and interspike intervals for the population of temporal patterns. As illustrated in FIG. 19A, an example temporal pattern is determined to possess a number of five pulses (e.g. spikes) and interspike intervals 3, 2, 3, and 5. FIG. 19B illustrates an example generation of temporal patterns and fitness values associated with each temporal pattern of the population. In this example, the number of spikes in each pattern may be determined. Continuing this example, the average fitness associated with each number of spikes is accumulated and an optimal number of spikes over time is determined.

FIG. 19C illustrates that the interspike intervals in each pattern of the population of temporal patterns is determined. In this example, the average fitness associated with each interpulse interval is accumulated and optimal interspike intervals over time is determined.

Figure 20:
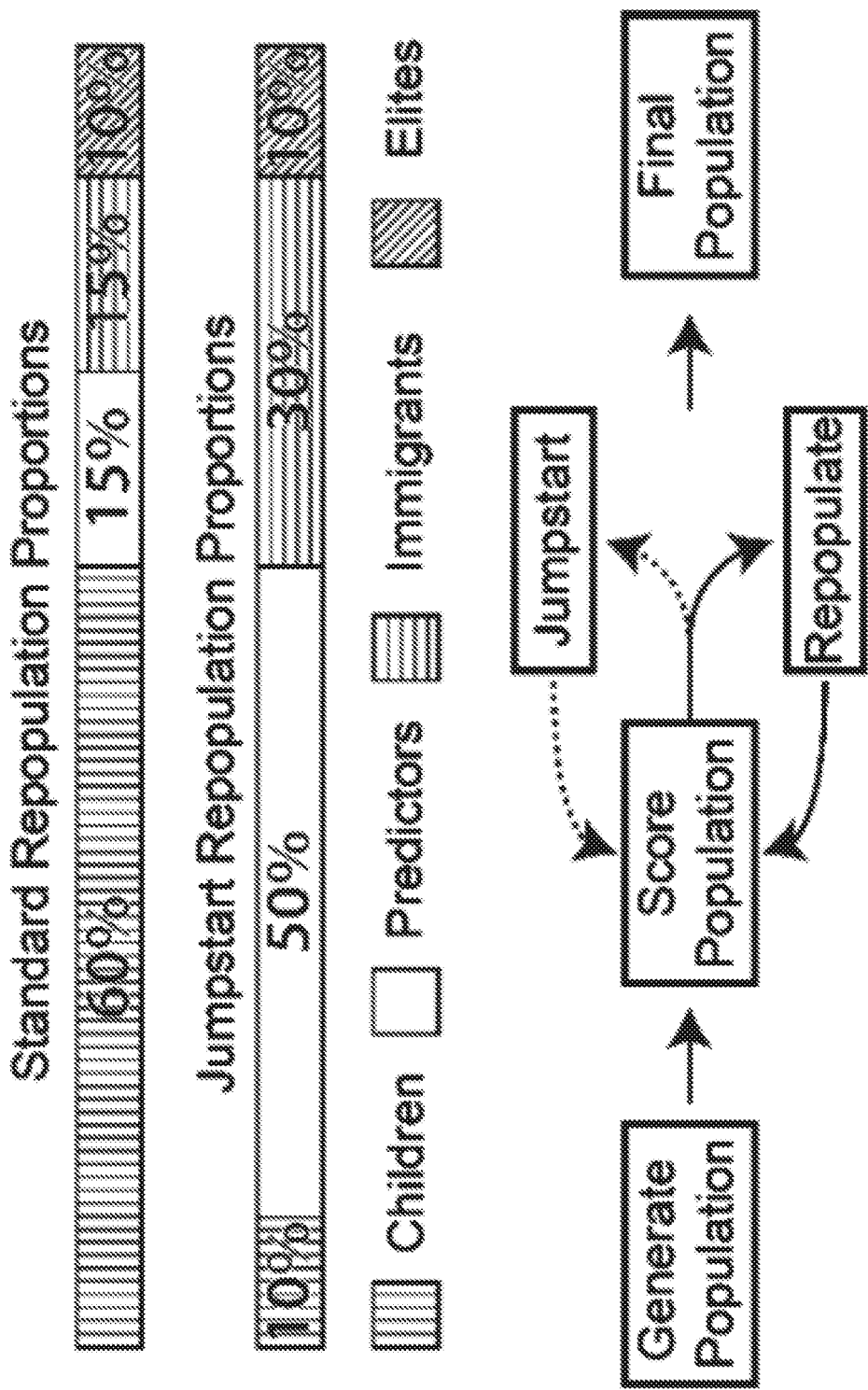
FIG. 20 is a graphical depiction of an example method of a jumpstart function in accordance with embodiments of the present disclosure.

Like many optimization algorithms GAs often identify local fitness maxima, and a Jumpstart (JS) function is disclosed herein to escape local maxima by replacing the standard repopulation method when the GA records the same maximum score for 20 consecutive generations. Jumpstart broadens the tested parameter space by reducing the proportion of new patterns that are produced via traditional mating between parents and replacing them with an increased number of PI and CI patterns to promote genetic diversity, as illustrated in FIG. 20. Jumpstart continues for a preset number of generations or until the population records a higher maximum score.

FIG. 20 illustrates an example method for the Jumpstart function in accordance with embodiments of the present disclosure. When the GA is stuck at a local maximum for a preset number of generations, Jumpstart increases the proportion of the next generation that are produced from PI and CI.

The effects of each modification individually, as well as their combinations, on the performance of the GA were evaluated first using test functions and subsequently using biophysically-based models of neural stimulation. To evaluate performance required hundreds of iterations of the GA, and each iteration (typically hundreds of generations) could take several days using biophysically-based neural models. Therefore, simpler test functions disclosed herein that required minimal computation but were sufficiently challenging to solve and contained multiple local maxima in addition to the global maximum. The functions were designed such that the worst and best solutions were known a priori, and all solutions were scaled on a zero (worst) to one (best) interval.

IPI fit was designed to mimic a scenario where the optimal stimulation pattern is composed of a few select IPI ranges. Each pattern was 450 bits long, and the function defined three ranges of IPIs with different number of points assigned to each of them: 15-17 (1 point), 30-32 (2.5 points), and 40-45 (3 points). Each stimulation pattern was then scored based upon the distribution of its respective IPIs across these ranges. In addition, to incentivize a lower average frequency of stimulation, the final score was divided by the weighted sum of the total number of pulses and the number of IPIs that did not fall into one of the three scoring ranges. It is noted that there are multiple local maxima but only one global maximum.

FIGS. 21A-21C illustrate simplified schematics of each of the test functions used to evaluate the modifications to the GA. FIG. 21A illustrates the interpulse interval (IPI) fit function design. Each pattern was first broken down into its component IPIs. Points were given for IPIs that fell within pre-defined ranges. The final score was weighted by the total number of pulses and normalized to one. FIG. 21B illustrates the refractory fit function. After the first pulse, a refractory period was randomly chosen. The next pulse in the pattern was found, and if it occurred after the refractory period it elicited an action potential and a new random refractory period, but if it occurred during the refractory period it did nothing. Points were given for each pulse that elicited an action potential and were taken away for each pulse that occurred during a refractory period. FIG. 21C illustrates the N-Queens Fit function to fit the maximum number of queens on a chessboard without any two of them being able to attack each other. The pattern was converted to placement of the queens, and points were given for each queen that could not attack another, and taken away for each that could.

Refractory fit aimed to mimic the neuronal refractory period, as illustrated in FIG. 21B, with the goal of stimulating a neuron as often as possible, but not within its refractory period. Each pattern was 450 bits long, with each bit of 1 representing a pulse at that time. After the first pulse, a refractory period was randomly chosen between 0 and 7 bits long. If the next pulse in the pattern occurred after the refractory period of the previous pulse, it elicited an "action potential" and was assigned a new, random refractory period. If the pulse occurred during the refractory period, it was not assigned a new refractory period. The fitness was calculated by adding a point each time an applied pulse caused an "action potential" and subtracting a point each time a pulse was delivered during a refractory period. Finally, the fitness was normalized to a 0-1 scale, with the maximum score assumed to be a pattern that had a pulse every 7 bits, thus never occurring during a refractory period. The order of assigned refractory periods varied randomly across generations, so optimized patterns had to respond robustly for the population to converge. This resulted in multiple local maxima, and no single pattern could be optimal across all generations of the GA.

The N-Queens Fit, as illustrated in FIG. 21C, is a common optimization problem to place the most queens on a chess board without any two of them able to attack each other. The chessboard was expanded to 30×30 squares to increase the difficulty, so each pattern was 900 bits long. Each pattern was first converted to locations on the chess board. One point was awarded for each queen on the board that could not be attacked, and one point was deducted for each queen that was threatened. Finally, each score was normalized to a 0-1 scale based on the known maximum number of queens, 30.

In addition to the three test functions, the modifications to the GA were tested on two biophysically-based computational models of neural stimulation: deep brain stimulation (DBS) in a network model of the cortical—basal ganglia—thalamic system and spinal cord stimulation (SCS) in a network model of the dorsal horn. In the model of the basal ganglia, the objective was to identify the temporal pattern of DBS that minimized both the signal power of neural activity in the beta frequency band (13-35 Hz) in the internal segment of the globus pallidus (GPi), as this is associated with symptoms of bradykinesia, and the average stimulation frequency, as this reduces energy demands of DBS. The fitness function was:

$$f = \frac{1000}{\text{Beta Power} + 3 \times \text{number of pulses}} \quad (1)$$

In the model of the dorsal horn, the objective was to identify a temporal pattern of SCS that reduced the average firing rate (AFR) of the model wide dynamic range neuron (WDR), as this is a proxy for the intensity of perceived pain and reduced the average stimulation frequency (ASF), which, as in DBS, can reduce stimulator energy requirements. The fitness function was:

$$f = \begin{cases} 20*(AFR-10)+(AFR-6.2)+(ASF-40) & \text{if } AFR > 10 \\ (AFR-6.2)+(ASF-40) & \text{otherwise} \end{cases} \quad (2)$$

The fitness is determined by comparison to the performance of 40 Hz SCS, which reduced AFR to 6.2 spikes/s, and the piecewise function was necessary because it did not matter how efficient the pattern of stimulation was if it did not sufficiently reduce WDR activity.

Two versions of the GA were run on each model: all modifications on and all modifications off In addition, for the modifications off condition, after 200 generations the modifications were all switched on and the algorithm was run for an additional 50-100 generations. Due to the computational demands of these models, the algorithms were run on a computing cluster.

The GA was run on the three test functions in two primary conditions: each modification individually added (Plus) and all modifications on with each modification individually removed (Minus). In both conditions, a no modifications was run on case (None) and an all modifications on case (All) to compare the results with. This strategy enabled determination of the effects of each modification individually, as well as in combination with the other modifications. For each condition, the GA was run with each of the three test functions for 200 iterations with 200 generations and a population size of 50 in each iteration. The best score for generations 50 and 200 were saved, which provided insight into the short-term convergence (generation 50) as well as the long-term optimal solution (generation 200) of the GA. A Kruskal-Wallis test was used to determine the effects of sample time and GA strategy on the normalized fitness. Then a Steel-Dwall's all pairs comparison was used to determine significance. The results reveal whether two distributions are significantly different from one another, and if so, which distribution has a higher value.

The performance of the GA across three test functions were evaluated. A standard algorithm (None), algorithms applying each modification individually (Plus), algorithms with all but one of the proposed modifications (Minus), and an algorithm were run that used all proposed modifications (All) for a total of 12 methodological variations. The score distribution of the GA variations was then compared across all three tests to draw conclusions about utility, and the performance was examined across individual tests for further insight into how each modification influenced performance.

Figure 22:
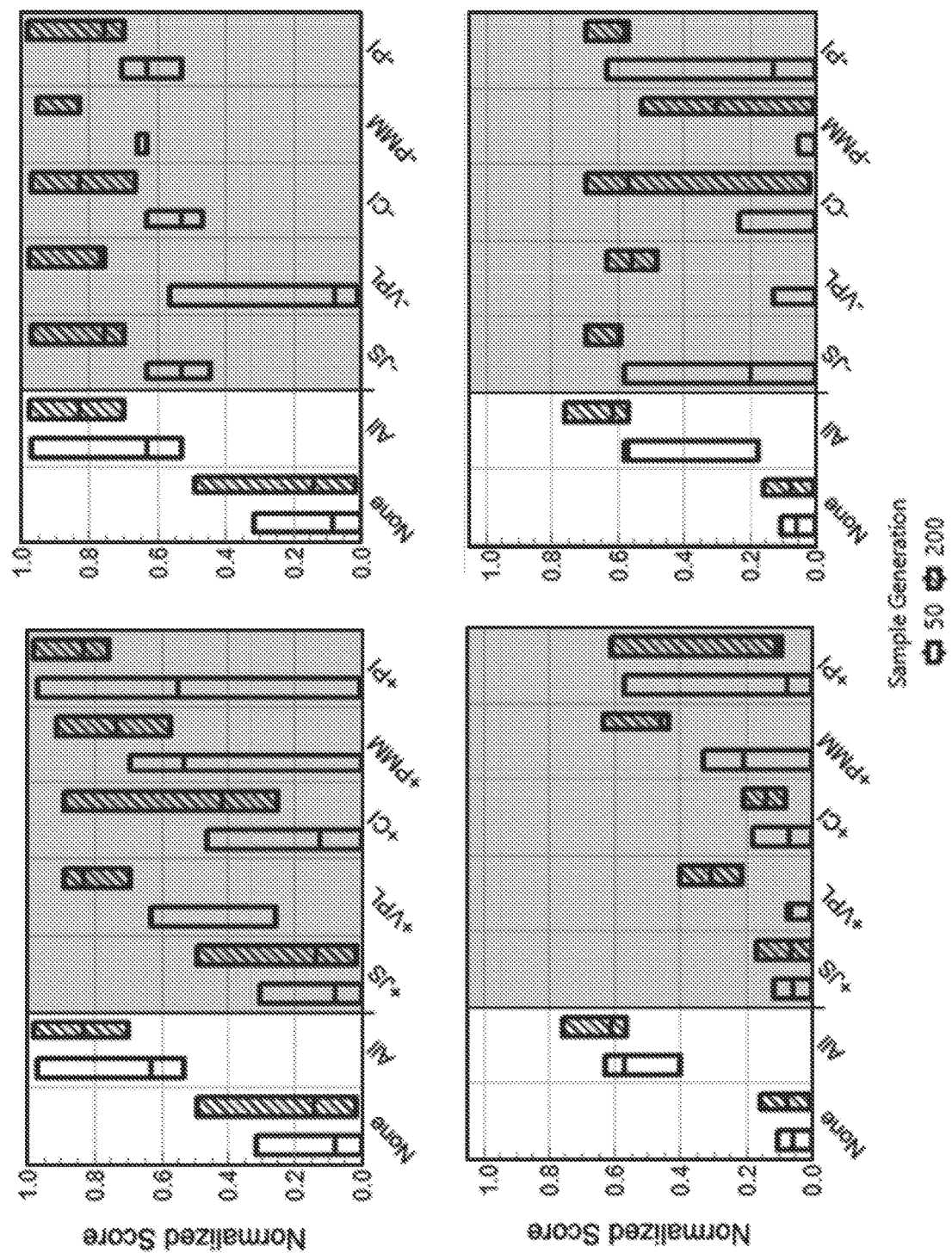
FIG. 22 is group of graphs depicting an example change in performance of the genetic algorithm from a jumpstart method, variable pattern length method, competitive immigrant method, pulse mutation method, and predictive immigrant method in accordance with embodiments of the present disclosure.

The minimum and median fitness values were averaged across the three test functions, as shown in FIG. 22. The median represents the most likely result of a single GA run, while the minimum shows the expected lower bound of a single GA run performance. The standard GA performed poorly, and the proposed modifications substantially increased the minimum and median fitness at both generation 50 and generation 200. When used individually (Plus), each of the modifications increased performance except for Jumpstart. In contrast, individual removal of each modification caused a substantial reduction in median and minimum fitness at generation 50 from the case with all modifications on. However, individual removal (Minus) of several modifications did not cause significant reductions in median and minimum fitness at generation 200, suggesting that performance may be saturated by generation 200. Finally, the All case exhibited the consistently highest median and minimum fitness, indicating the robustness of the proposed modifications.

FIG. 22 illustrates changes in performance of the GA from each of the proposed modifications: jumpstart (JS), variable pattern length (VPL), competitive immigrants (CI), pulse mutation method (PMM), and predictive immigrants (PI), combined across the three test functions. Since there are only three scores, the bounds of the box and the line are at the values of the three scores. (a,b) The medians of each test function at generation 50 and 200. The top left graph is the Plus case, in which each modification was added individually, and the top right graph is the Minus case, in which all modifications were turned on, and then removed individually. The lower graphs show the minimums in each test function at generation 50 and 200. The lower left graph is the Plus case, in which each modification was added individually, and the lower right graph is the Minus case, in which all modifications were turned on, and then removed individually.

Figure 23:
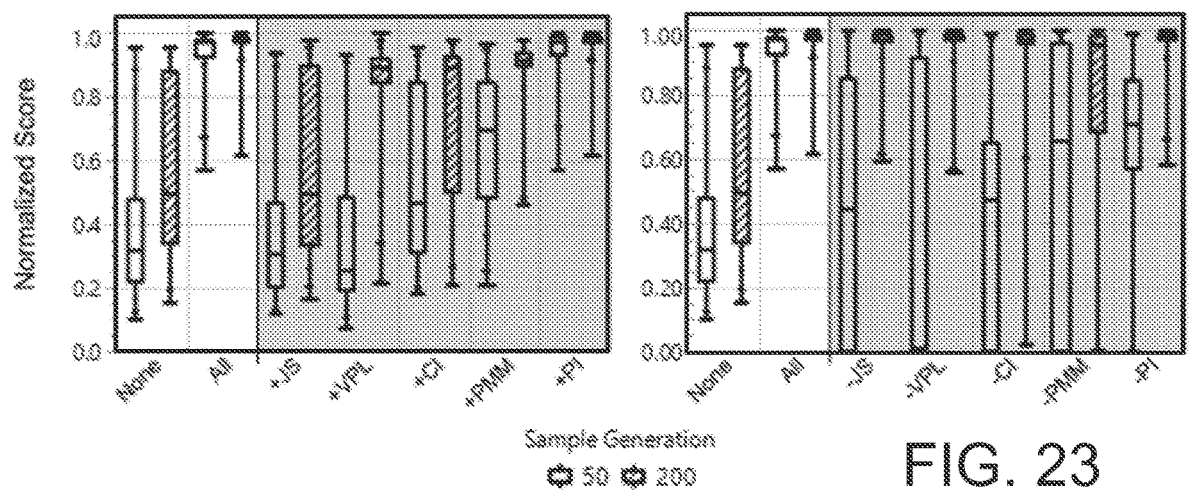
FIG. 23 is a group of graphs depicting an example change in performance of the genetic algorithm using the interpulse interval fit function in accordance with embodiments of the present disclosure.

When collectively used, the proposed modifications increased the median fitness scores on the IPI Fit task from 0.32 and 0.49 to 0.97 and 0.98 at generations 50 and 200, respectively, and led to approximately five-fold increases in the minimum fitness scores as shown in Table 1 and the left graph of FIG. 23 shows a dramatic increase in the short-term speed of the GA and the consistency of the algorithm across runs. The inclusion, as shown in the left graph of FIG. 23 of CI, PMM, and PI each individually improved performance from the baseline GA at both generations 50 and 200. VPL did not affect performance at generation 50, but greatly increased performance by generation 200, and JS did not result in an improvement. Removing individually any of the GA modifications, as shown in the right graph of FIG. 23 reduced the fitness scores; these effects were most pronounced at generation 50, and by generation 200 the median fitness was not influenced with JS, VPL or CI removed, although the minimum fitness scores were lower.

FIG. 23 illustrates changes in performance from the proposed modifications to the GA on the Interpulse Interval Fit function. The left graph shows normalized fitness from the Plus case, where each modification was added individually. The right graph shows normalized from the Minus case, where all modifications were turned on, and then removed individually. Results from 200 replicates are shown as quartile box-and-whisker plots where whiskers extend to the absolute minimum and maximum, the box covers the interquartile range of scores, and the line is the median

TABLE 1

Statistics for the Interpulse Interval Fit results.

| Strategy | None | | JS | | VPL | | CI | | PMM | | PI | | All | |
|---|---|---|---|---|---|---|---|---|---|---|---|---|---|---|
| Generation | 50 | 200 | 50 | 200 | 50 | 200 | 50 | 200 | 50 | 200 | 50 | 200 | 50 | 200 |
| Plus | N/A | N/A | + | − | + | ++ | ++ | ++ | ++ | ++ | ++ | ++ | ++ | ++ |
| Minus | ++ | ++ | ++ | − | ++ | + | ++ | − | ++ | ++ | ++ | ++ | N/A | N/A |

Effect on performance: + +, significantly improves; +, improves; −, reduces; − −, significantly reduces score.

The All case increased the median scores from 0 and 0.02 to 0.63 and 0.83 at generation 50 and 200 respectively as shown in Table 2 and FIG. 24, and once again substantially increased the minimum scores. Removing the JS and PMM modifications did not affect performance by generation 50, and removing CI did not significantly affect the performance at either generation 50 or 200. However, removing each modification substantially decreased the minimum score even if it did not significantly affect the distribution.

Figure 24:
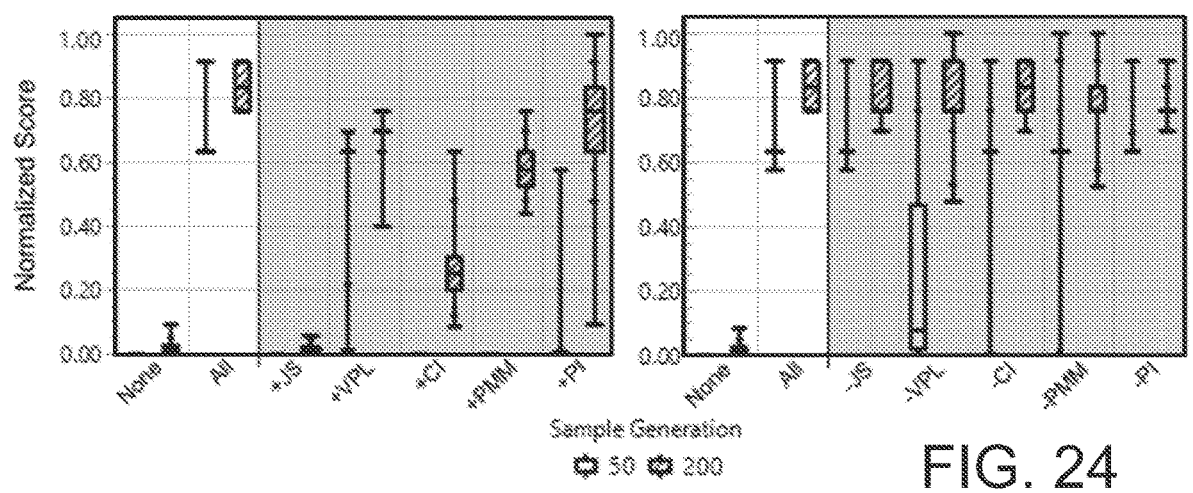
FIG. 24 is a group of graphs depicting an example change in performance of the genetic algorithm using the refractory fit function in accordance with embodiments of the present disclosure.

FIG. 24 illustrates changes in performance from the proposed modifications to the GA on the refractory fit function. The left graph shows normalized fitness from the Plus case, where each modification was added individually. The right graph shows normalized fitness from the Minus case, where all modifications were turned on, and then removed individually. Results from the 200 trials are shown as quartile box-and-whisker plots where whiskers extend to the absolute minimum and maximum, the box covers the interquartile range of scores, and the line is the median score.

Figure 25:
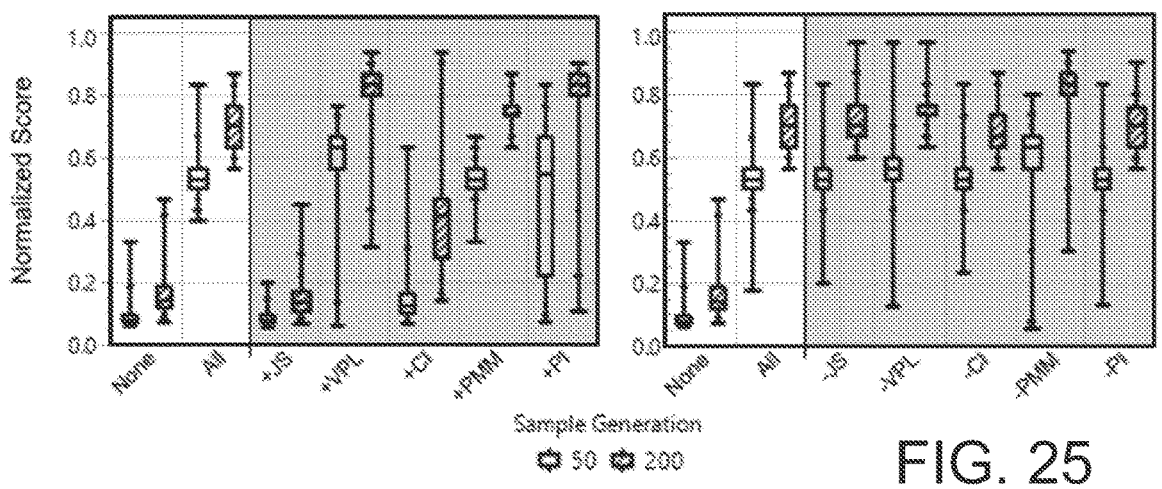
FIG. 25 is a group of graphs depicting an example change in performance of the genetic algorithm using the N-Queens fit function in accordance with embodiments of the present disclosure.

The proposed modifications in the All case dramatically increased the median scores from 0.08 and 0.14 to 0.53 and 0.70 at generations 50 and 200, respectively as shown in Table 3 and FIG. 25. This difference is further highlighted by the substantially different minimum values.

TABLE 2

Statistics for the Refractory Fit results.

| Strategy | None | | JS | | VPL | | CI | | PMM | | PI | | All | |
|---|---|---|---|---|---|---|---|---|---|---|---|---|---|---|
| Generation | 50 | 200 | 50 | 200 | 50 | 200 | 50 | 200 | 50 | 200 | 50 | 200 | 50 | 200 |
| Plus | N/A | N/A | − | − | ++ | ++ | ++ | ++ | ++ | ++ | ++ | ++ | ++ | ++ |
| Minus | ++ | ++ | − | ++ | ++ | ++ | − | + | + | ++ | ++ | ++ | N/A | N/A |

Effect on performance: + +, significantly improves; +, improves; −, reduces; − −, significantly reduces Individually, the PMM modification matched the performance of all the modifications combined, and the VPL outperformed the All case. On the other hand, removing either of these two modifications resulted in significantly higher scores, indicating that these modifications were negatively affecting performance. Only when removing the CI modification were scores reduced, and only at generation 200.

FIG. 25 illustrates changes in performance from the proposed modifications to the GA on the N-Queens Fit function. The left graph of FIG. 25 shows normalized fitness from the Plus case, where each modification was added individually. The right graph of FIG. 25 shows normalized fitness from the Minus case, where all modifications were turned on, and then removed individually. The results from the 200 trials are shown as quartile box-and-whisker plots where whiskers extend to the absolute minimum and maximum, the box covers the interquartile range of scores, and the line is the median score.

TABLE 3

Statistics for the N-Queens Fit results.

| Strategy | None | | JS | | VPL | | CI | | PMM | | PI | | All | |
|---|---|---|---|---|---|---|---|---|---|---|---|---|---|---|
| Generation | 50 | 200 | 50 | 200 | 50 | 200 | 50 | 200 | 50 | 200 | 50 | 200 | 50 | 200 |
| Plus | N/A | N/A | − | − | ++ | ++ | ++ | ++ | ++ | ++ | ++ | ++ | ++ | ++ |
| Minus | ++ | ++ | − | − | −− | −− | + | ++ | −− | −− | + | − | N/A | N/A |

Figure 26A:
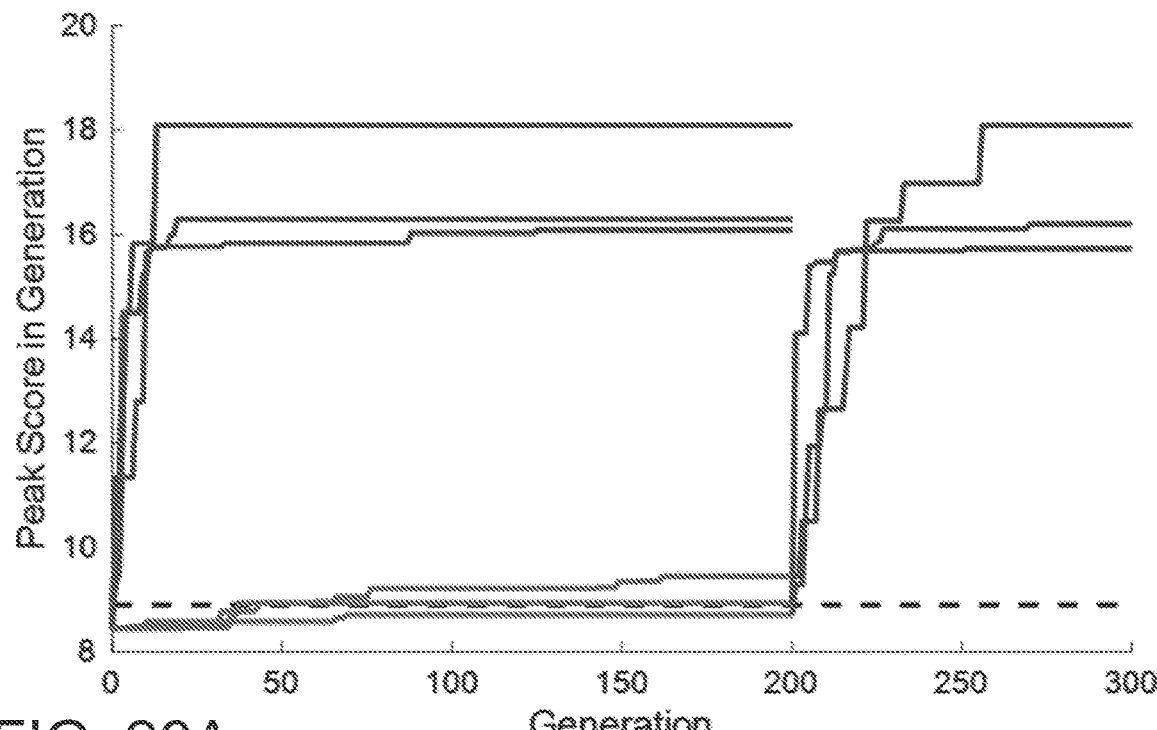
FIG. 26A is a graph of example results from applying the genetic algorithm of the present disclosure to a network model of a basal ganglia-thalamus-cortex to optimize temporal patterns of DBS in accordance with embodiments of the present disclosure.

Effect on performance: + +, significantly improves; +, improves; −, reduces; − −, significantly reduces The proposed modifications to the GA increased the rate of convergence of the GA and resulted in temporal patterns of DBS with higher fitness values than the standard GA, as illustrated in FIG. 26A. The proposed modifications also rescued populations that had converged to suboptimal patterns, as shown by the consistent and dramatic increase in fitness when the modifications were switched on after the standard GA had converged.

Figure 26B:
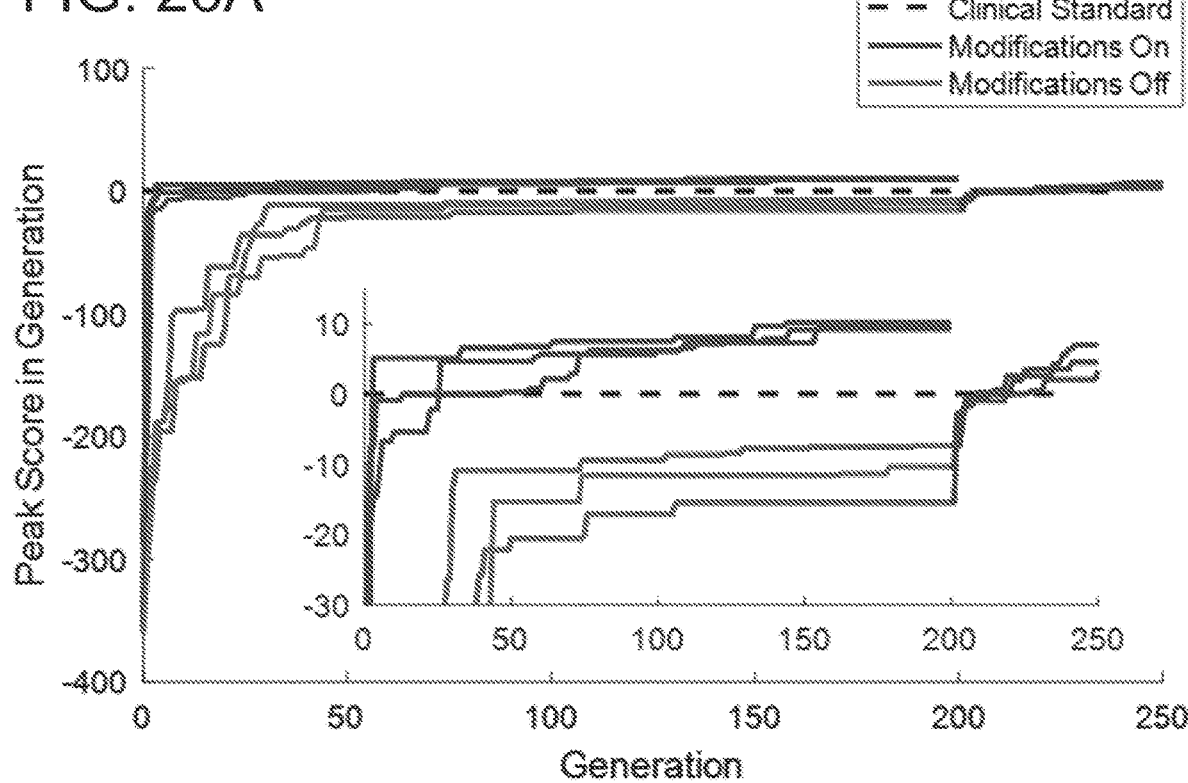
FIG. 26B is graph of example results from applying the genetic algorithm of the present disclosure to a network model of the spinal dorsal horn to optimize temporal patterns of SCS in accordance with embodiments of the present disclosure.

Fitness scores in the SCS model were compared to the fitness of standard 40 Hz SCS, which was consistently the highest performing constant frequency pattern. The proposed modifications increased the rate of convergence and resulted in temporal patterns of SCS with higher fitness values, as illustrated in FIG. 26B. Further, when the modifications were turned on after the standard GA had plateaued, the fitness once again rapidly increased.

FIGS. 26A and 26B illustrate changes in fitness across generations of the GA for the two biophysically-based models of neural stimulation. As shown in FIG. 26A, results from applying the GA to a network model of the basal ganglia-thalamus-cortex to optimize temporal patterns of DBS. As shown in FIG. 26B, results from applying the GA to a network model of the spinal dorsal horn to optimize temporal patterns of SCS. The inset shows just the results scoring between −30 and 10. For each model, GAs were run under two conditions: modifications on (blue) and modifications off (red) for 200 generations. For the modifications off condition, after the 200 generations the modifications were turned on (blue). Also plotted is the score for a clinically standard, constant frequency stimulation (black dash): 130 Hz for FIG. 26A and 40 Hz for FIG. 26B.

The disclosed modifications to the standard GA method can increase the rate of convergence and the final solution fitness across both a standardized set of evaluation tasks and two applications relevant to the design of temporal patterns of neural stimulation. Although the impact of individual modifications varied across tasks, we suggest applying all the proposed modifications simultaneously as this approach consistently exhibited high median and minimum values. Further, there were apparent synergistic effects of some of the proposed modifications. For example, Jumpstart provided no measurable utility when implemented alone, but when it was removed from the complete set, the rate of convergence was negatively affected. Since every possible combination of the individual modifications was not observed, it is possible that a limited combination of modifications may, depending on the task, perform better than applying all of them together.

The pulse mutation method modification was highly successful in each of the three test functions. Its primary effect was to reduce the variance of the trials, but at the cost of reducing the fitness of some of the top performing trials. PMM statistically matched the performance of the combined modifications on the N-Queens test, but removing it improved the GA performance. This paradoxical effect may be explained by the design of the modification. PMM prevented changes to the average number of pulses as a result of mutation, and while this seems to be beneficial for poorly performing solutions, it appears that preferentially adding pulses benefits highly performing solutions. This explanation is consistent across the solutions of all three tests, but is most exemplified by the N-Queens test, possibly because it is not based on neuromodulation principles.

As expected, competitive immigrants consistently reduced the variance of the solutions. This modification resulted in slowly converting the immigrants into a string of consecutive point mutations over time, which may explain why the effect varied between tests. A string of mutations is more likely to be useful in the IPI and N-Queens Fits, where score changes can be localized to a subsection of the solution vector, as opposed to refractory fit, where a local change affects how the pattern is scored across the entire solution.

The variable pattern length modification improved performance for all but the combined modifications N-Queens test. This implies that it had a strong negative interaction with at least one other modification. It may be that the negative interaction was with the PI. Both can solve the N-Queens problem alone, but neither benefited the combined modifications scores. Varying the pattern length only improves the GA methodology in cases where inferences about the total solution can be drawn from smaller segments. However, because the PI depends heavily on IPIs, the combination of these strategies may be finding high performing local maxima but reducing the final fitness.

The predictive immigrants modification is clearly one of the most effective improvements. It is not surprising that the PI was highly effective at the IPI fit function, because both operate using the interpulse intervals of a pattern. However, PI also improved performance for both the refractory fit and N-Queens fit. Neither of these explicitly used interpulse intervals, and yet PI successfully increased the score when implemented individually for both.

Jumpstart is seemingly the least effective of the improvements. When implemented individually, it has no measurable effect on any of the fit functions. However, it is noted that JS is designed to be used when the GA gets stuck at local maxima. In the None case, the standard GA performed poorly, and changing the population proportions using Jumpstart had negligible effect. The minus cases are more illustrative of Jumpstart's benefit, as these cases test whether it provides any performance improvement to GAs that retain diverse competition when approaching local maxima. In addition, Jumpstart has no effect if the algorithm continuously makes incremental improvements, so it has more of an impact if the solutions saturates near the optimum, which is more common in the Minus cases.

Although the arbitrary fit functions provide clear insight into the efficacy of the proposed modifications, the performance of the GA on biophysically-based computational models provided compelling support for the modified methodology. In both models, the modified GA not only reached substantially higher final fitness than the standard GA, but it did so in many fewer generations. Furthermore, when the modifications were added to the GA after the standard methodology had converged, the algorithm rapidly converged to a new solution with much higher fitness.

In addition to the fitness scores of the final generation patterns, FIGS. 27A and 27B show the raster plots of a representative subset of the stimulation trains resulting from the modified and standard GA applied to the dorsal horn model. Both algorithms converged to non-regular patterns of stimulation, which emphasizes the necessity and design utility of a GA. Without the modifications, when the fitness plateaued the population had converged to a single solution. The random immigrants, while introducing diversity, may not be selected as parents for the next generation as their fitness is no longer competitive. Further, the children of the previous generation are barely distinguishable from the elites, and thus two-point cross-over mating will do little to further explore the solution space. However, the modified GA identified solutions with substantially higher fitness and greater diversity of pulse timing. This diversity contributes to avoiding local maxima and thus identifying patterns with greater fitness.

FIGS. 27A and 27B illustrate raster plots of a representative subset of the stimulation patterns in the final generation of standard GA with FIG. 27A illustrating modifications off and FIG. 27B illustrating modifications on applied to the network model of the dorsal horn. The y-axis gives the fitness score for each pattern.

GAs can determine optimal solutions both quickly and effectively, and binary GAs are particularly well suited to identifying optimal temporal patterns of neural stimulation. The proposed modifications: pulse mutation, competitive immigrants, variable pattern length, predictive immigrants, and jumpstart, substantially improved the performance of the standard GA, and their combination was highly effective across multiple test functions, including application to biophysically-based computational models of neuromodulation. This improved genetic algorithm provides a robust method for finding optimal temporal patterns of stimulation.

GA can be implemented on an external computer and a computational model of the neurological system is used to determine the neurological system response to the pattern of stimulation. A measurement of neural activity within the computational model is used as a proxy for the predicted effects on symptoms of a temporal pattern of stimulation. The value of the proxy is then used within the cost function or fitness function to determine the performance of the pattern of stimulation.

GA can also be implemented within the implanted pulse generator implanted surgically in the patient. This can be achieved via either a remote (e.g., wireless, RF, transcutaneous) connection from a computer to the implanted stimulator, or internalizing the algorithm to execute within the implantable pulse generator (IPG). In this implementation measurements are made from the patient to assess the effect of a particular pattern of stimulation on symptoms. Such measurements could include, for example, an accelerometer signal to measure tremor, electromyographic signals to assess muscle activity, recordings of biopotential signals (e.g., local field potentials or single neuron spiking activity) to determine neural activity, or direct patient reports via indications entered for example on a key pad, for example ratings of pain perception levels. In this implementation measurements may also be made from the patient to assess the effect of a particular pattern of stimulation on side effects using similar measurement or reporting systems. In an alternative implementation measurements are made from the patient to assess the effect of a particular pattern of stimulation on symptoms and side effects by another individual, for example a health care professional, and could include objective symptom scoring (for example, the unified Parkinson's disease rating scale or tremor rating scale). The value(s) of these measurement(s) are then used within the cost function or fitness function to determine the performance of the pattern of stimulation.

There were several aspects of the PI modification that we could manipulate individually, so we examined interactions of these methodologies to determine the best strategy for the GA. We have four versions: PI-1 is the base version, banding and repeat are additions to PI-1, and PI-2 is PI-1 with both expand and repeat added. Averaging the medians across the different fit functions showed differences in the different PI versions after 50 and 200 generations as shown in FIG. 28A. When added individually, as shown in FIG. 28A, PI-2 did not seem to be any superior to PI-1+Repeat. However, when the PI versions were added to the GA with the other modifications also on, as shown in FIG. 28B, Repeat appeared to have a negative interaction with the other modifications, producing a worse score at generation 50 than PI-1. However, PI-2 produces the best scores after both 50 and 200 generations, indicating that Repeat and Banding may have a synergistic effect when the other modifications are present.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While certain embodiments have been described, these embodiments have been presented by way of example only, and are not intended to limit the scope of the inventions. Indeed, the novel methods, devices, and systems described herein may be embodied in a variety of other forms. Furthermore, various omissions, substitutions, and changes in the form of the methods, devices, and systems described herein may be made without departing from the spirit of the inventions. The accompanying claims and their equivalents are intended to cover such forms or modifications as would fall within the scope and spirit of the inventions.

What is claimed:

1. A method comprising:
   selecting a temporal pattern for neural stimulation;
   determining a mutation type for altering a pattern of pulses of the temporal pattern;
   identifying a location within the pattern of pulses of the temporal pattern to alter based on the determined mutation type; and
   altering the pattern of pulses of the temporal pattern based on the identified location and mutation type for application of the altered pattern of pulses of the temporal pattern to a subject.

2. The method of claim 1, wherein selecting the temporal pattern comprises selecting a pattern of pulses for stimulation of neurons.

3. The method of claim 1, wherein determining the mutation type comprises at least one of adding a pulse to the pattern of pulses of the temporal pattern or removing a pulse from the pattern of pulses of the temporal pattern.

4. The method of claim 1, wherein identifying the location within the pattern of pulses of the temporal pattern comprises randomly identifying a location to alter within the pattern of pulses.

5. The method of claim 1, wherein identifying the location within the pattern of pulses of the temporal pattern comprises:
   determining that the location within the pattern of pulses cannot be altered based on the mutation type; and
   in response to determining that the location within the pattern of pulses cannot be altered, selecting another location to alter within the pattern of pulses to alter based on the mutation type.

6. The method of claim 1, further comprising selecting a predetermined number of locations to alter within the pattern of pulses.

7. The method of claim 1, wherein altering the pattern of pulses comprises altering the pattern of pulses while maintaining an average frequency of the temporal pattern.

8. The method of claim 1, further comprising adding the altered pattern of pulses of the temporal pattern to a population of temporal patterns of neural stimulation.

9. The method of claim 1, further comprising applying the altered temporal pattern of neural stimulation to a computational model.

10. The method of claim 1, further comprising using a neural stimulation device to apply the altered temporal pattern to the subject.

11. A computing device comprising:
    a temporal pattern selection unit comprising at least one processor and memory configured to:
    select a temporal pattern for neural stimulation;
    determine a mutation type for altering a pattern of pulses of the temporal pattern;
    identify a location within the pattern of pulses of the temporal pattern to alter based on the determined mutation type; and alter the pattern of pulses of the temporal pattern based on the identified location and mutation type for application of the altered pattern of pulses of the temporal pattern to a subject.

12. The computing device of claim 11, wherein the temporal pattern selection unit is configured to select a pattern of pulses for stimulation of neurons.

13. The computing device of claim 11, wherein the temporal pattern selection unit is configured to at least one of adding a pulse to the pattern of pulses of the temporal pattern or removing a pulse from the pattern of pulses of the temporal pattern.

14. The computing device of claim 11, wherein the temporal pattern selection unit is configured to:
   determine that the location within the pattern of pulses cannot be altered based on the mutation type; and
   select another location to alter within the pattern of pulses to alter based on the mutation type in response to determining that the location within the pattern of pulses cannot be altered.

15. The computing device of claim 11, wherein the temporal pattern selection unit is configured to elect a predetermined number of locations to alter within the pattern of pulses.

16. The computing device of claim 11, wherein the temporal pattern selection unit is configured to alter the pattern of pulses while maintaining an average frequency of the temporal pattern.

17. The computing device of claim 11, wherein the temporal pattern selection unit is configured to add the altered pattern of pulses of the temporal pattern to a population of temporal patterns of a computational model of neural stimulation.

18. The computing device of claim 11, wherein the temporal pattern selection unit is configured to apply the altered temporal pattern of neural stimulation to a computational model.

19. The computing device of claim 11, further comprising a neural stimulation device configured to apply the altered temporal pattern to the subject.

20. A computer program product comprising a computer readable storage medium having program instructions embodied therewith, the program instructions executable by a computing device to cause the computing device to:
   select, by the computing device, a temporal pattern for neural stimulation;
   determine, by the computing device, a mutation type for altering a pattern of pulses of the temporal pattern;
   identify, by the computing device, a location within the pattern of pulses of the temporal pattern to alter based on the determined mutation type; and
   alter, by the computing device, the pattern of pulses of the temporal pattern based on the identified location and mutation type for application of the altered pattern of pulses of the temporal pattern to a subject.

* * * * *